United States Patent
Arora et al.

(10) Patent No.: US 10,815,240 B2
(45) Date of Patent: Oct. 27, 2020

(54) MANUFACTURING PROCESS AND INTERMEDIATES FOR A PYRROLO[2,3-D]PYRIMIDINE COMPOUND AND USE THEREOF

(71) Applicant: Pfizer Inc., New York, NY (US)

(72) Inventors: Kapildev Kashmirilal Arora, Niantic, CT (US); Jacob Cole DeForest, Pawcatuck, CT (US); Andrew Kevern Hills, Sandwich (GB); Brian Patrick Jones, Waterford, CT (US); Kris Nicole Jones, Waterford, CT (US); Chad Arthur Lewis, Salem, CT (US); Anil Mahadeo Rane, Mystic, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 16/502,703

(22) Filed: Jul. 3, 2019

(65) Prior Publication Data

US 2020/0123159 A1    Apr. 23, 2020

Related U.S. Application Data

(60) Provisional application No. 62/855,071, filed on May 31, 2019, provisional application No. 62/776,642, filed on Dec. 7, 2018, provisional application No. 62/694,698, filed on Jul. 6, 2018.

(51) Int. Cl.
*C07D 487/04* (2006.01)
*C07D 249/08* (2006.01)

(52) U.S. Cl.
CPC ......... *C07D 487/04* (2013.01); *C07D 249/08* (2013.01); *C07B 2200/13* (2013.01)

(58) Field of Classification Search
CPC .................................................. C07D 487/04
USPC ........................................................ 544/280
See application file for complete search history.

(56) References Cited

U.S. PATENT DOCUMENTS 3,773,919 A    11/1973    Boswell et al.
4,485,045 A    11/1984    Regen
4,544,545 A    10/1985    Ryan et al.
5,013,556 A    5/1991    Woodle et al.
2014/0243312 A1    8/2014    Brown et al.

FOREIGN PATENT DOCUMENTS

JP    2000-128867    5/2000
WO    2011/017800 A1    2/2011
WO    2016/024185 A1    2/2016

OTHER PUBLICATIONS

Caira, "Crystalline Polymorphism of Organic Compounds", Topics in Current Chemistry 198:163-208 (1998).
Database Registry [Online]; Chemical Abstracts Service, Columbus, Ohio, US; Aug. 18, 2006 (Aug. 18, 2006), Database Accession No. 902708-70-7.
Database Registry [Online]; Chemical Abstracts Service, Columbus, Ohio, US; May 24, 2006 (May 24, 2006), Database Accession No. 885434-77-5.
Friedman et al, "Structure activity optimization of 6H-pyrrolo[2,3-e][1,2,4]triazolo[4,3-a]pyrazines as Jak1 kinase Inhibitors", Bioorganic & Medicinal Chemistry Letters 25(20):4399-4404 (2015).
PCT International Search Report and Written Opinion for International Application No. PCT/IB2019/055683 dated Oct. 25, 2019.
Sharghi et al, "An overview on recent advances in the synthesis of sulfonated organic materials, sulfonated silica materials, and sulfonated carbon materials and their catalytic applications in chemical processes", Beilstein Journal of Organic Chemistry 14:2745-2770 (2018).
Vazquez et al, "Identification of N-{cis-3-[Methyl(7H-pyrrolo[2,3-d]pyrimidin-4-yl)amino]cyclobutyl}propane-1-sulfonamide (PF-04965842): A Selective JAK1 Clinical Candidate for the Treatment of Autoimmune Diseases", Journal of Medicinal Chemistry 61(3):1130-1152 (2018).
Finnin et al, "Transdermal Penetration Enhancers: Applications, Limitations, and Potential", Journal of Pharmaceutical Sciences 88(10):955-958 (1999).

*Primary Examiner* — Jeffrey H Murray
(74) *Attorney, Agent, or Firm* — A. David Joran

(57) ABSTRACT

The present invention relates to a manufacturing process and intermediates for preparing a crystalline or non-crystalline form of N-((1S,3S)-3-(methyl(7H-pyrrolo[2,3-d]pyrimidin-4-yl)amino)cyclobutyl)propane-1-sulfonamide. The present invention also relates to salt forms and pharmaceutical compositions comprising the crystalline form, and to methods for use of the compound prepared from a crystalline form in the treatment of various diseases.

2 Claims, 13 Drawing Sheets

Specification includes a Sequence Listing.

MANUFACTURING PROCESS AND INTERMEDIATES FOR A PYRROLO[2,3-D]PYRIMIDINE COMPOUND AND USE THEREOF

RELATED APPLICATIONS

This application claims the benefit of U.S. Provisional Application No. 62/694,698, filed Jul. 6, 2018; U.S. Provisional Application No. 62/776,642, filed Dec. 7, 2018; and U.S. Provisional Application No. 62/855,071, filed May 31, 2019, which are hereby incorporated by reference in their entireties.

SEQUENCE LISTING

This application is being filed electronically via EFS-Web and includes an electronically submitted sequence listing in .txt format. The .txt file contains a sequence listing entitled "PC72459A_Sequence_Listing_ST25_06202019.txt" created on Jun. 20, 2019, and having a size of 38 KB. The sequence listing contained in this .txt file is part of the specification and is incorporated herein by reference in its entirety.

FIELD OF THE INVENTION

The present invention relates to a manufacturing process and intermediates for preparing a crystalline or non-crystalline form of N-((1S,3S)-3-(methyl(7H-pyrrolo[2,3-d]pyrimidin-4-yl)amino)cyclobutyl)propane-1-sulfonamide. The present invention also relates to pharmaceutical compositions comprising the crystalline form, and to methods for use of the crystalline form in the treatment of various diseases.

BACKGROUND OF THE INVENTION

N-((1S,3S)-3-(Methyl(7H-pyrrolo[2,3-d]pyrimidin-4-yl)amino)cyclobutyl)propane-1-sulfonamide has the chemical formula $C_{14}H_{21}N_5O_2S$ and the following structural formula:

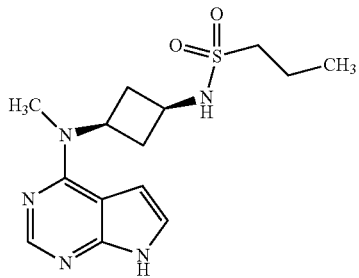 [SMILES: CCCS(=O)(=O)N[C@H]1C[C@@H](N(C)c2ncnc3[nH]ccc23)C1]

A preparative synthesis of N-((1S,3S)-3-(methyl(7H-pyrrolo[2,3-d]pyrimidin-4-yl)amino)cyclobutyl)propane-1-sulfonamide is described in commonly assigned U.S. Pat. No. 9,035,074, the contents of which are incorporated herein by reference in their entirety. The crystalline form of N-((1S,3S)-3-(methyl(7H-pyrrolo[2,3-d]pyrimidin-4-yl)amino)cyclobutyl)propane-1-sulfonamide free base, is useful as an inhibitor of protein kinases, such as the enzyme Janus Kinase (JAK) and as such is useful therapeutically as an immunosuppressive agent for organ transplants, xenotransplantation, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia and other indications where immunosuppression would be desirable. The present invention relates to a manufacturing process and intermediates for preparing a crystalline or non-crystalline form of N-((1S,3S)-3-(methyl (7H-pyrrolo[2,3-d]pyrimidin-4-yl)amino)cyclobutyl)propane-1-sulfonamide, whereby the crystalline form provides certain improved properties for use in manufacture of a pharmaceutical dosage form, particularly for oral and topical dosage forms.

SUMMARY OF THE INVENTION

The present invention is directed to a process for preparing a crystalline or noncrystalline form of N-((1S,3S)-3-(methyl(7H-pyrrolo[2,3-d]pyrimidin-4-yl)amino)cyclobutyl)propane-1-sulfonamide free base. The invention is also directed to compositions, including pharmaceutical compositions, containing the crystalline 3-((3R,4R)-4-methyl-3-[methyl-(7H-pyrrolo[2,3-d]pyrimidin-4-yl)amino]piperidin-1-yl)-3-oxopropionitrile free base. The present invention also provides a method of treating a disease in a mammal, comprising administering to a mammal in need thereof a therapeutically effective amount of crystalline N-((1S,5S)-3-(methyl(7H-pyrrolo[2,3-d]pyrimidin-4-yl)amin-o)cyclobutyl)propane-1-sulfonamide or a pharmaceutically acceptable salt thereof or a pharmaceutical composition, said disease being selected from rheumatoid arthritis, lupus, psoriasis, atopic dermatitis, vitiligo and inflammatory bowel disease.

DETAILED DESCRIPTION OF THE INVENTION

Figure 1:
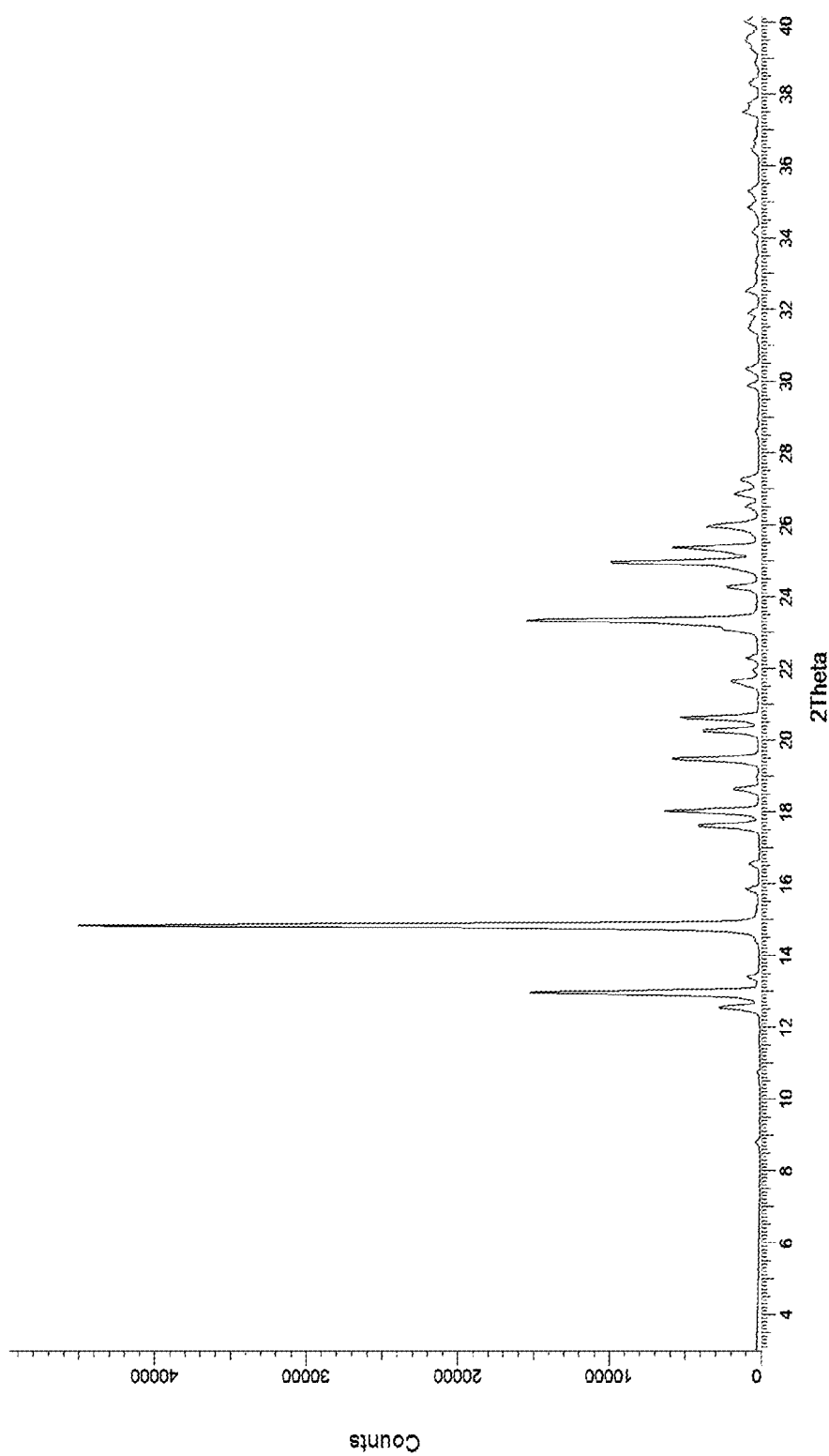
FIG. 1 depicts a powder X-ray diffraction pattern of the crystalline form of N-((1S,3S)-3-(methyl(7H-pyrrolo[2,3-d]pyrimidin-4-yl)amino)cyclobutyl)propane-1-sulfonamide.
Figure 2:
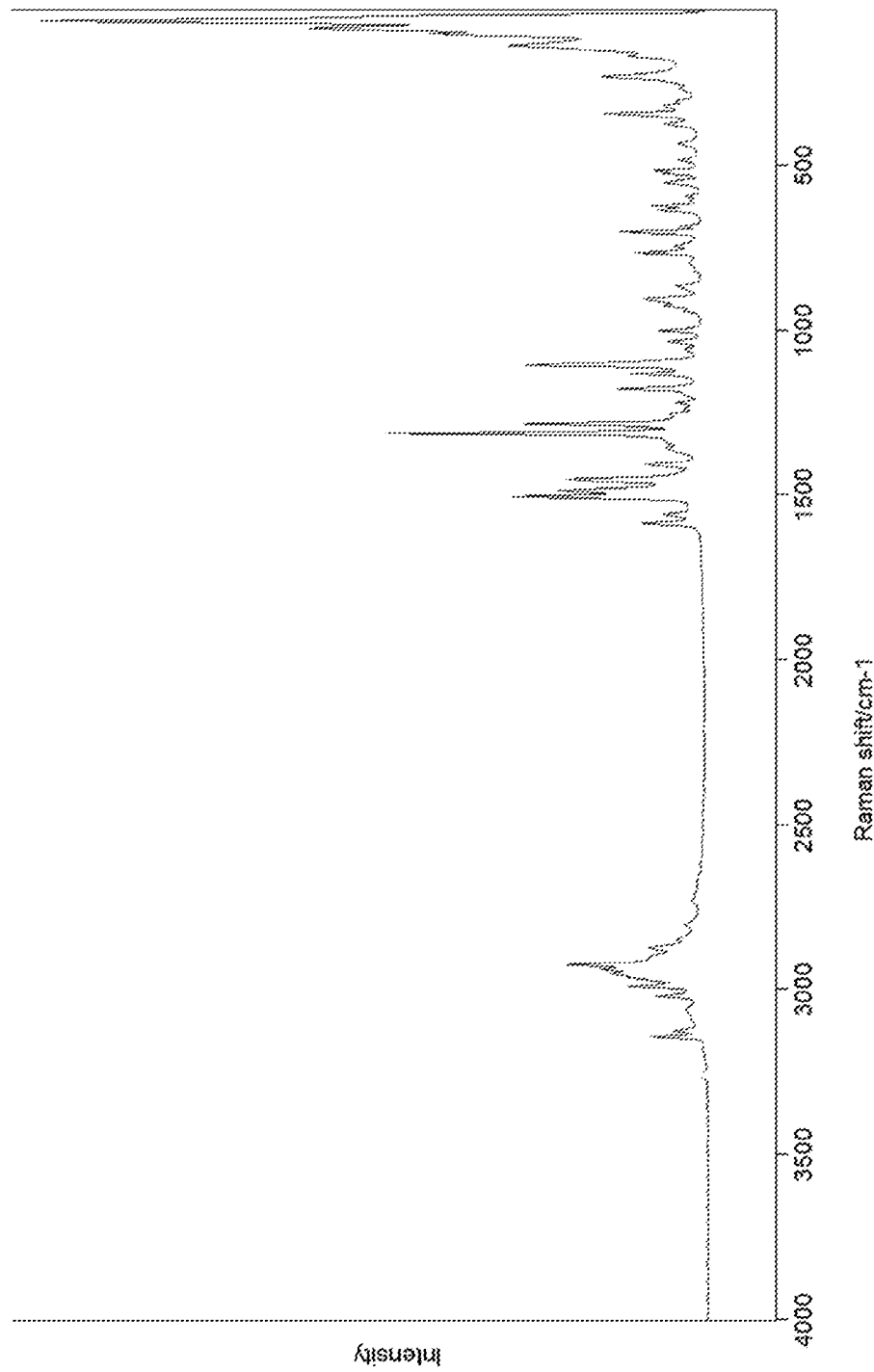
FIG. 2 depicts a Raman spectrum of the crystalline form of N-((1S,3S)-3-(methyl(7H-pyrrolo[2,3-d]pyrimidin-4-yl)amino)cyclobutyl)propane-1-sulfonamide.
Figure 3:
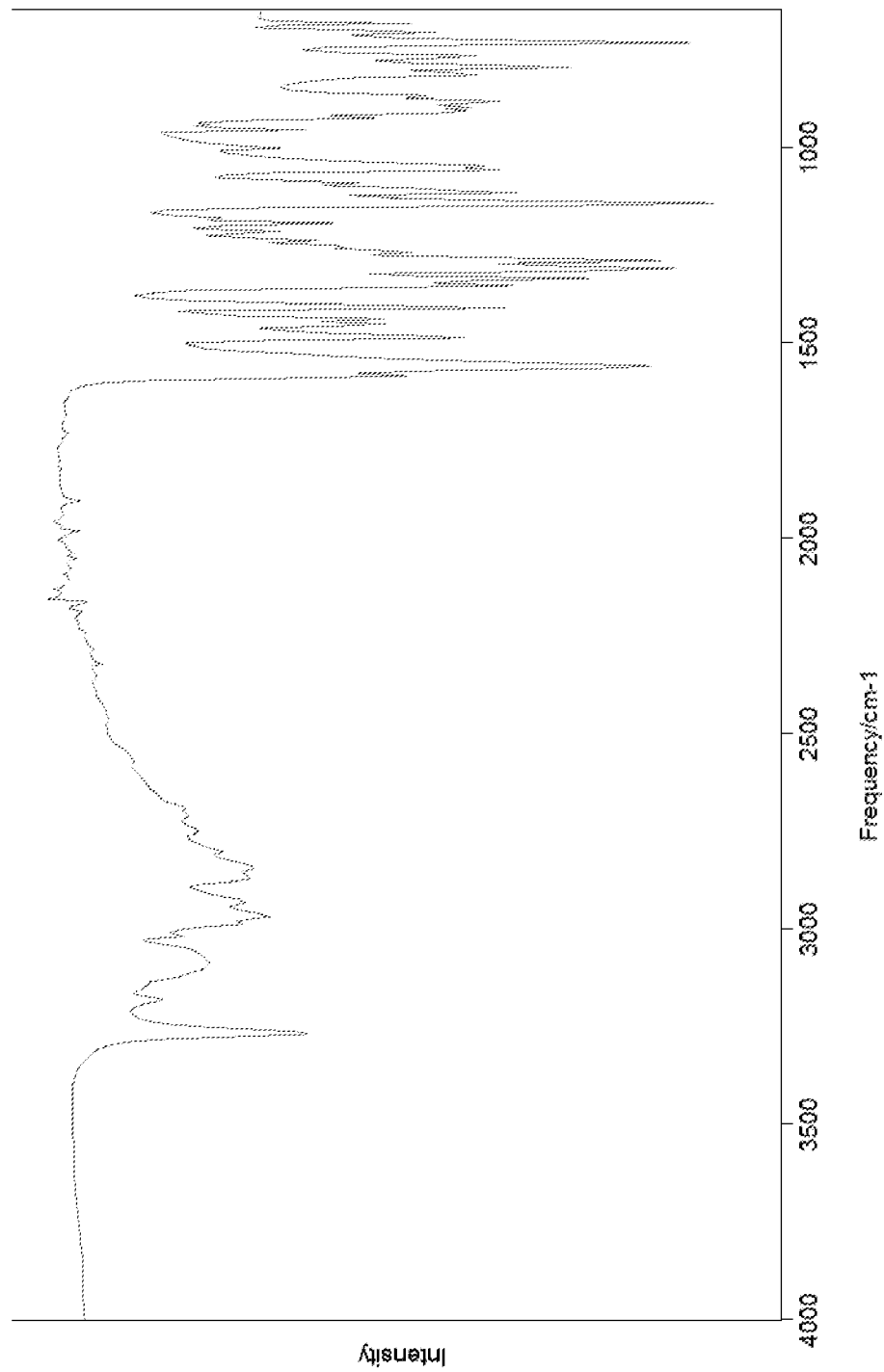
FIG. 3 depicts a FT-IR spectrum of the crystalline form of N-((1S,3S)-3-(methyl(7H-pyrrolo[2,3-d]pyrimidin-4-yl)amino)cyclobutyl)propane-1-sulfonamide.
Figure 4:
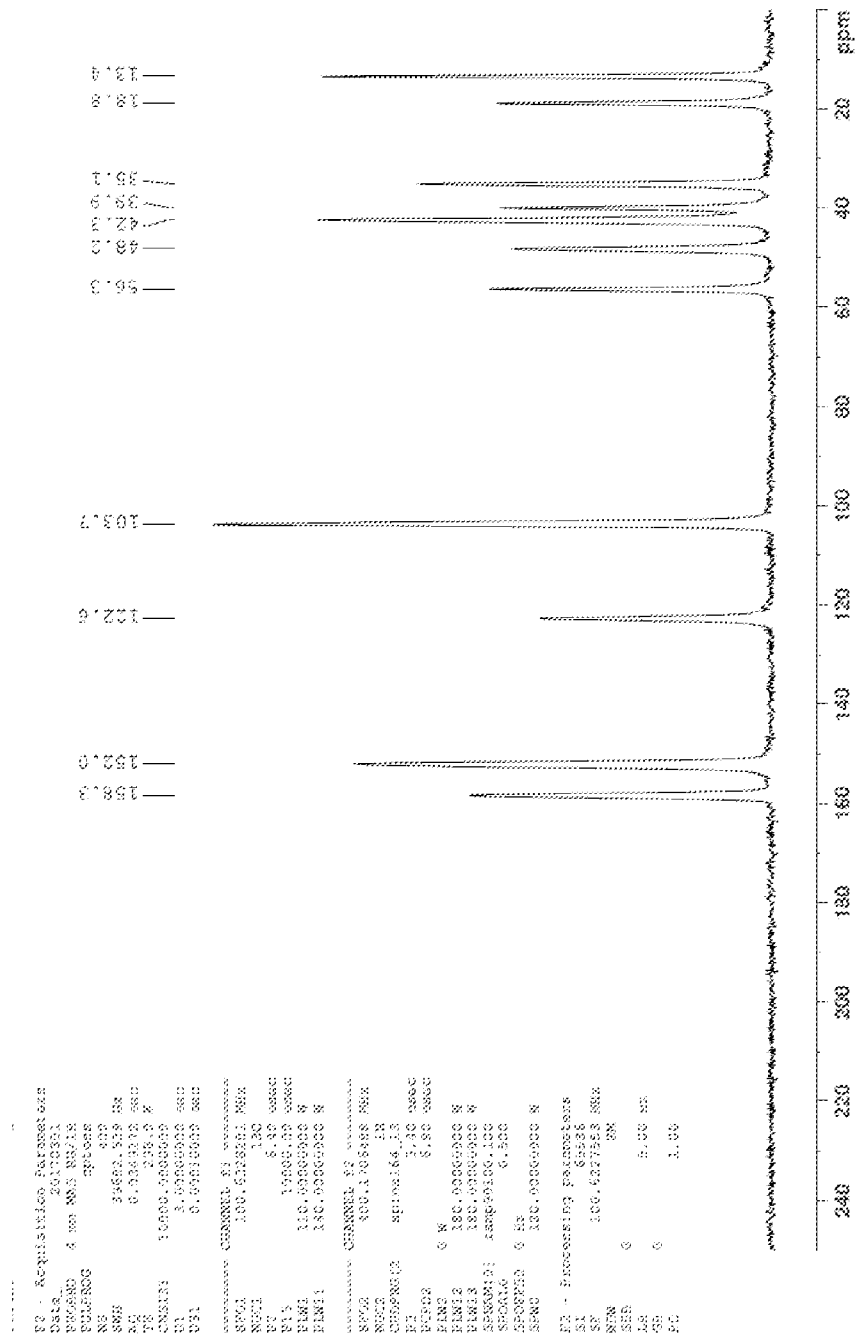
FIG. 4 depicts a solid state $^{13}C$ nuclear magnetic resonance spectrum of the crystalline form of N-((1S,3S)-3-(methyl(7H-pyrrolo[2,3-d]pyrimidin-4-yl)amino)cyclobutyl)propane-1-sulfonamide. Spinning sidebands are noted with an asterisk.
Figure 5:
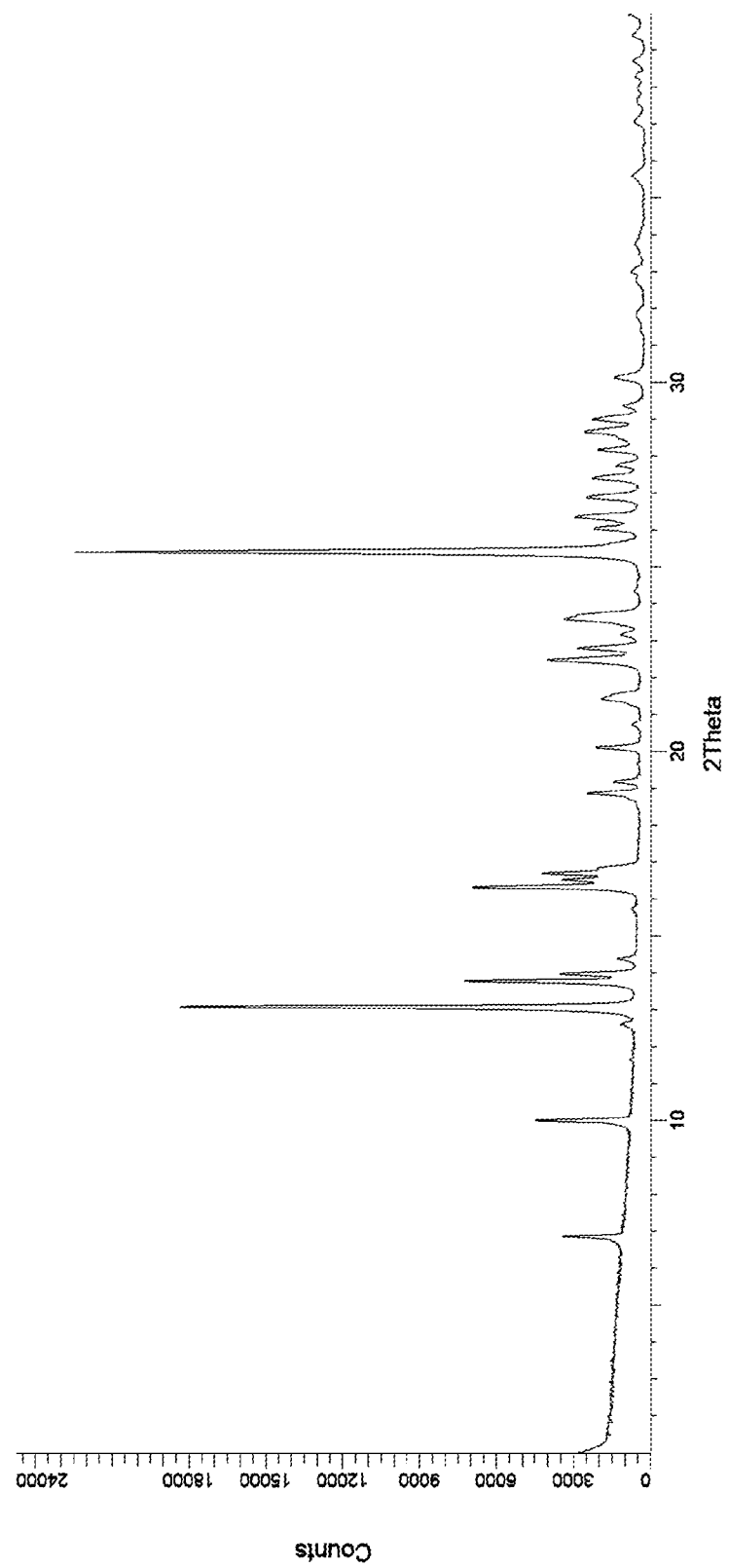
FIG. 5 depicts a powder X-ray diffraction pattern of the crystalline form of N-((1S,3S)-3-(methyl(7H-pyrrolo[2,3-d]pyrimidin-4-yl)amino)cyclobutyl)propane-1-sulfonamide Form A, mono HCl anhydrous.
Figure 6:
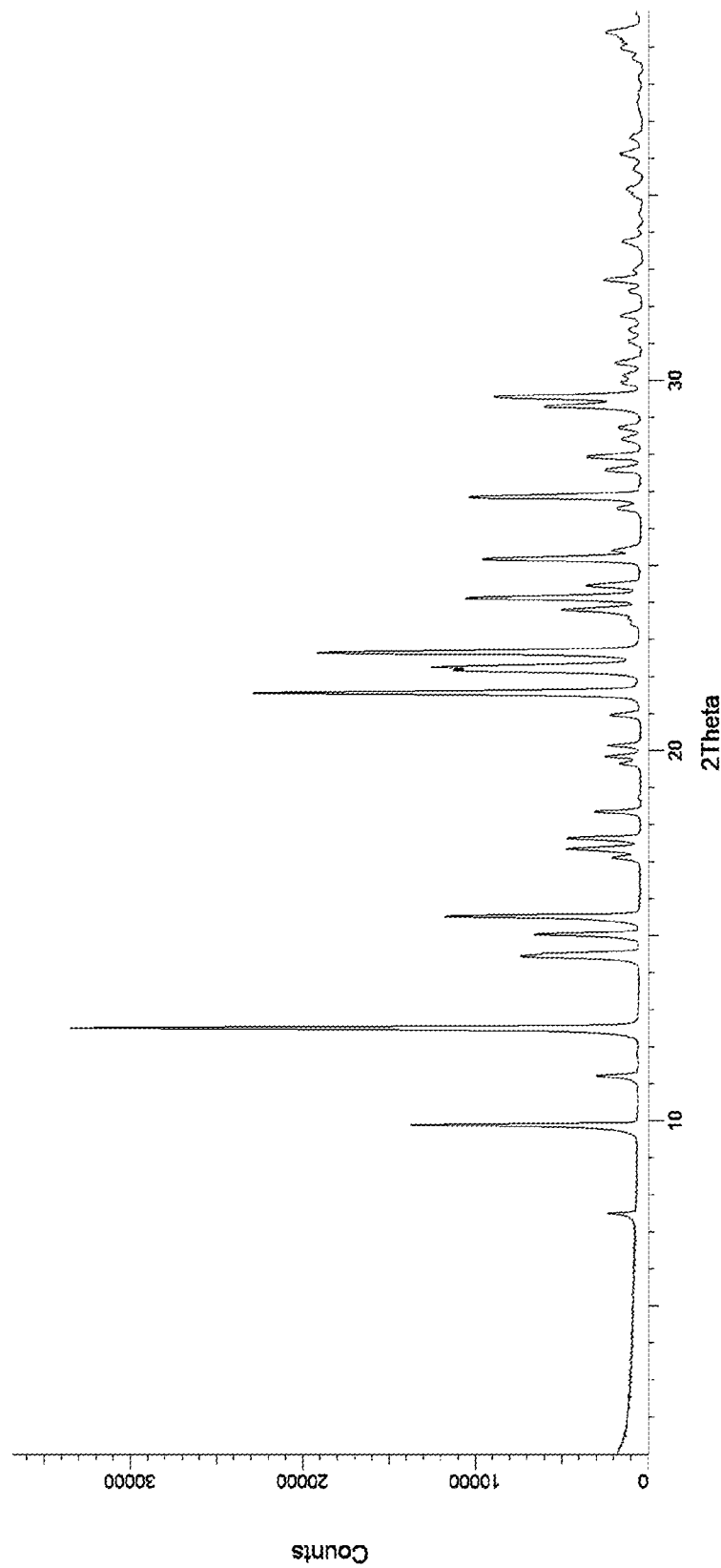
FIG. 6 depicts a powder X-ray diffraction pattern of the crystalline form of N-((1S,3S)-3-(methyl(7H-pyrrolo[2,3-d]pyrimidin-4-yl)amino)cyclobutyl)propane-1-sulfonamide Form B, mono HCl monohydrate.
Figure 7:
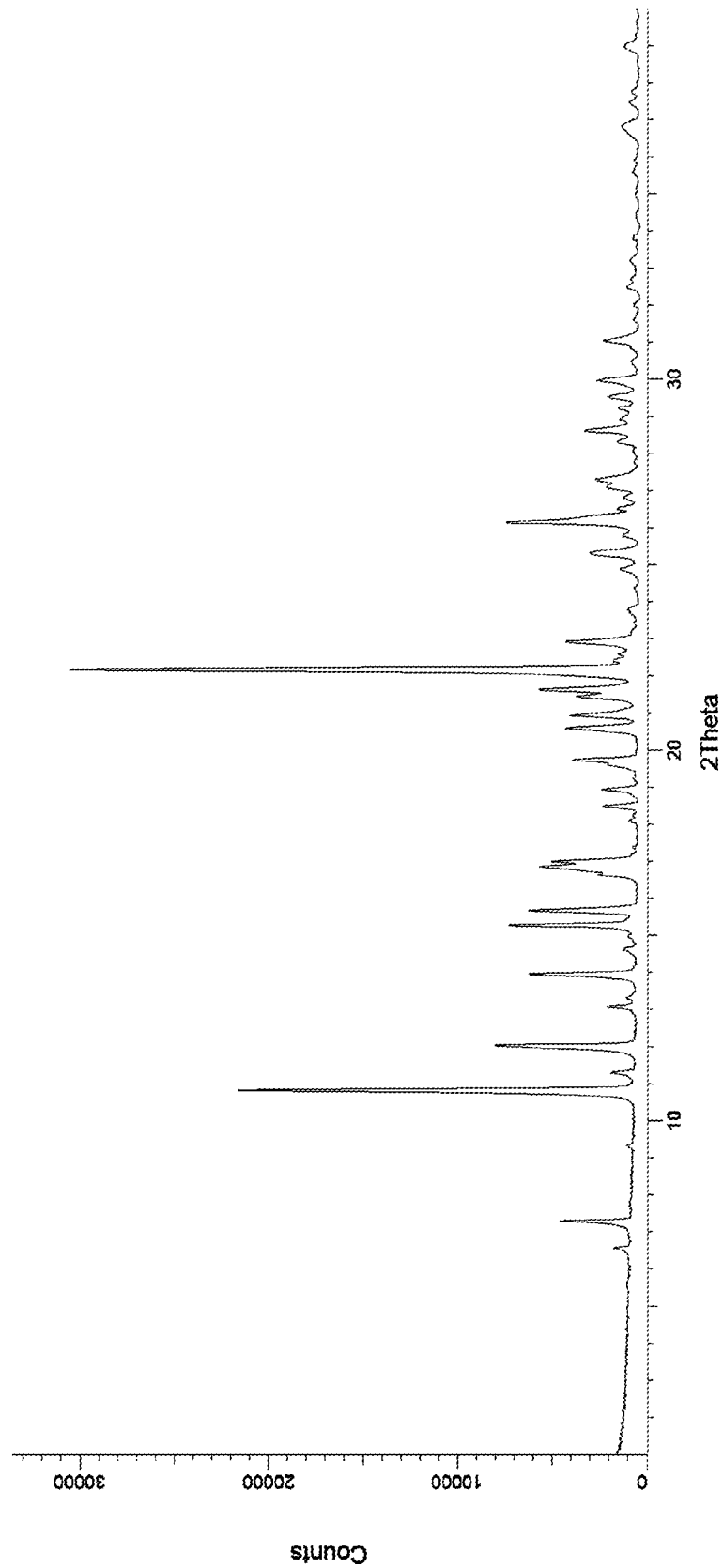
FIG. 7 depicts a powder X-ray diffraction pattern of the crystalline form of N-((1S,3S)-3-(methyl(7H-pyrrolo[2,3-d]pyrimidin-4-yl)amino)cyclobutyl)propane-1-sulfonamide Form C, mono HCl anhydrous.
Figure 8:
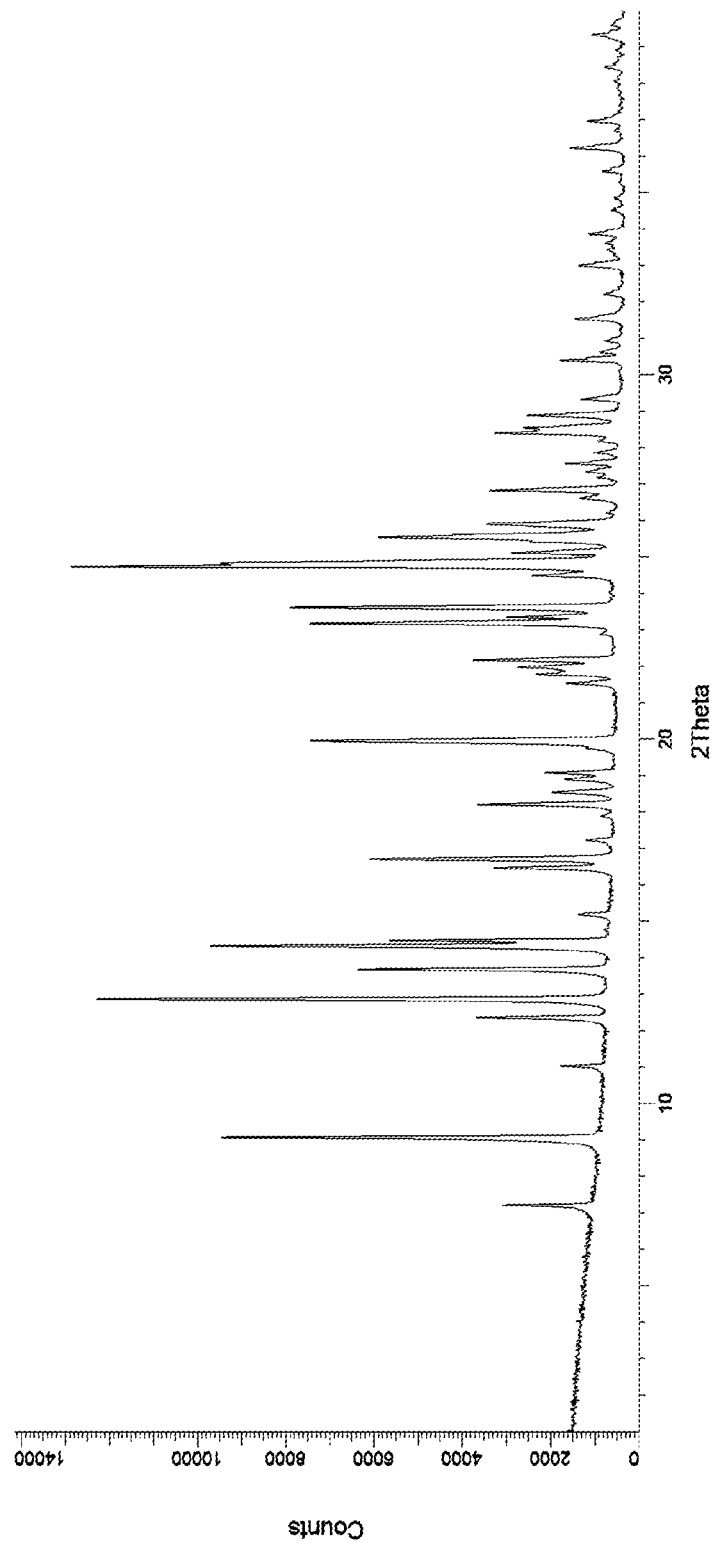
FIG. 8 depicts a powder X-ray diffraction pattern of the crystalline form of N-((1S,3S)-3-(methyl(7H-pyrrolo[2,3-d]pyrimidin-4-yl)amino)cyclobutyl)propane-1-sulfonamide Form E, mono HCl dihydrate.
Figure 9:
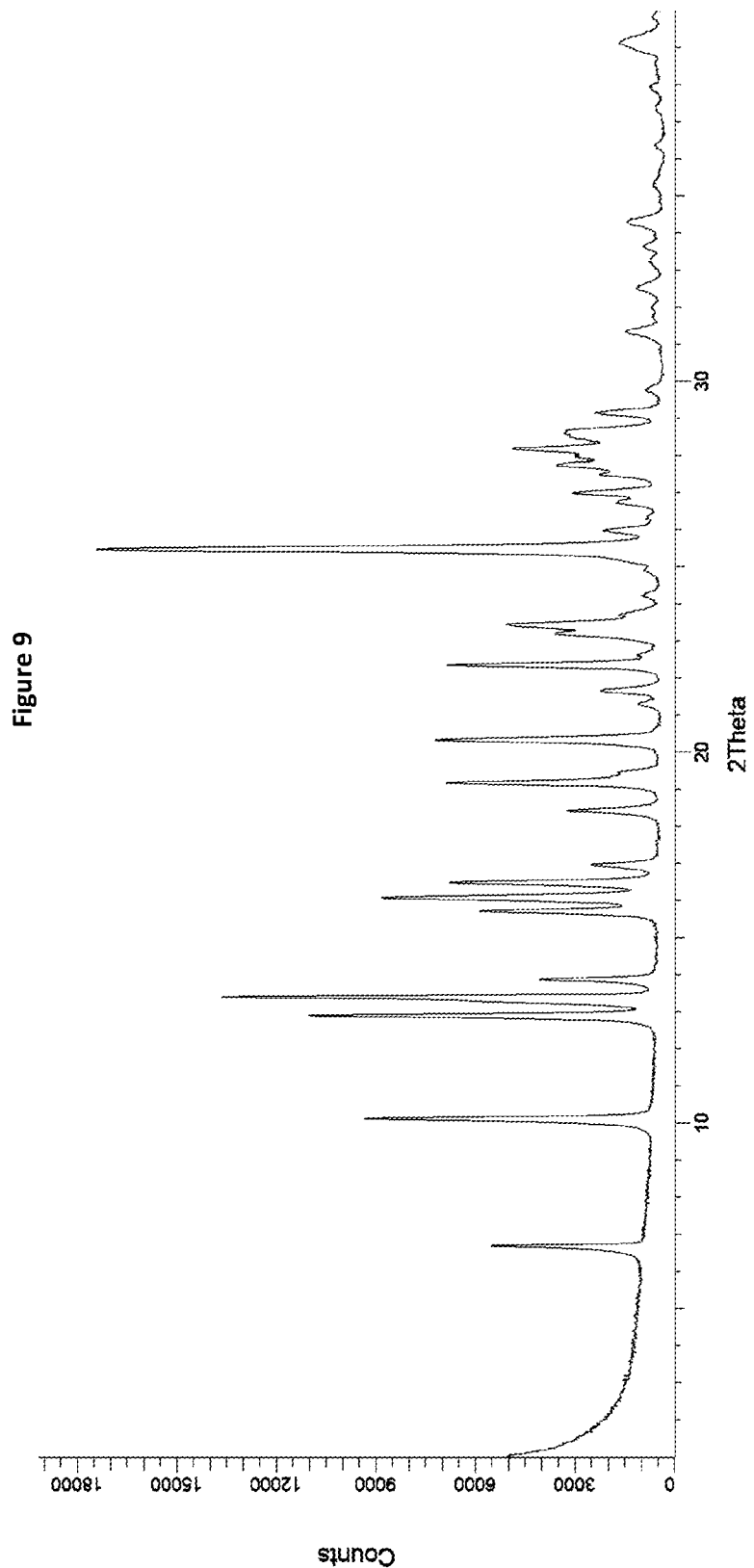
FIG. 9 depicts a powder X-ray diffraction pattern of the crystalline form of N-((1S,3S)-3-(methyl(7H-pyrrolo[2,3-d]pyrimidin-4-yl)amino)cyclobutyl)propane-1-sulfonamide Form G, mono HCl anhydrous.
Figure 10:
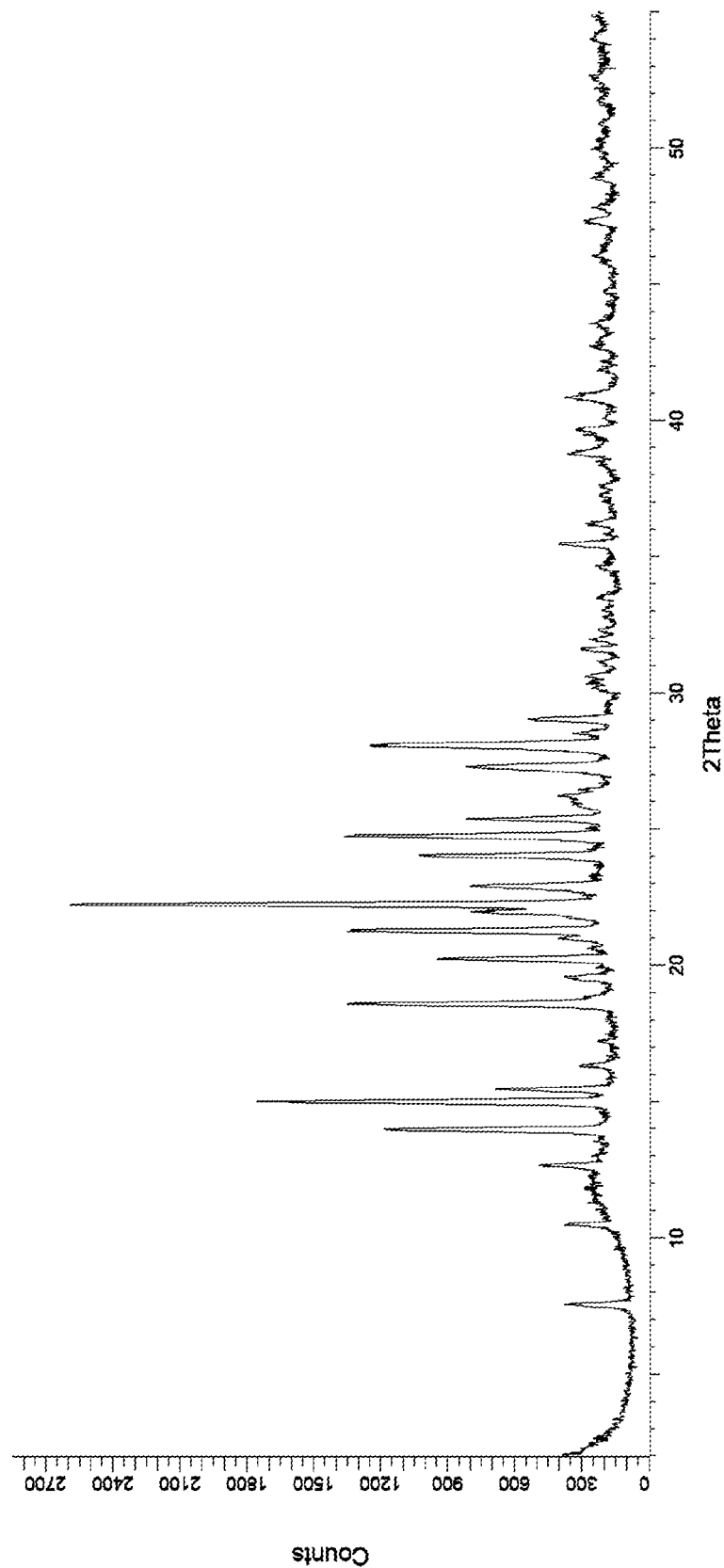
FIG. 10 depicts a powder X-ray diffraction pattern of the crystalline form of N-((1S,3S)-3-(methyl(7H-pyrrolo[2,3-d]pyrimidin-4-yl)amino)cyclobutyl)propane-1-sulfonamide hemisulfate salt.
Figure 11:
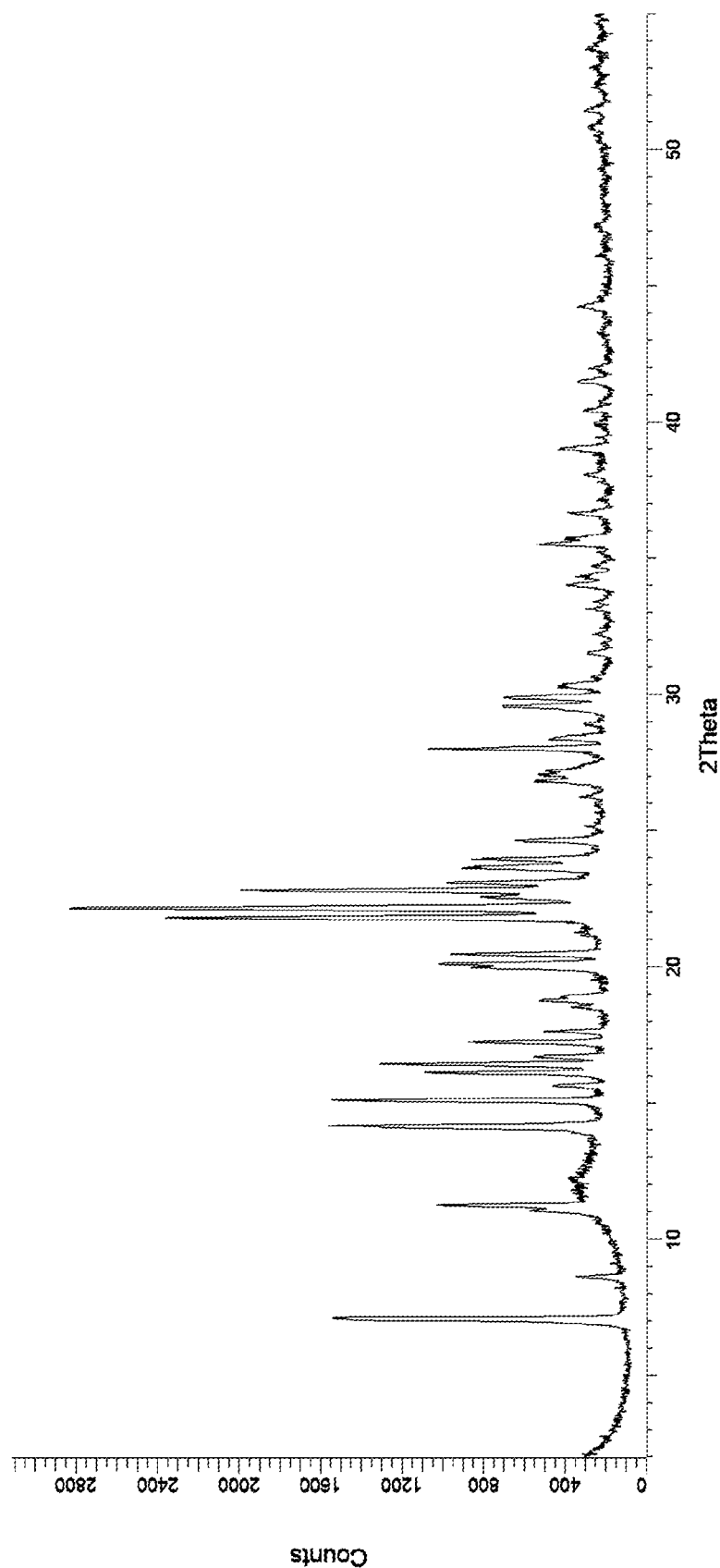
FIG. 11 depicts a powder X-ray diffraction pattern of the crystalline form of N-((1S,3S)-3-(methyl(7H-pyrrolo[2,3-d]pyrimidin-4-yl)amino)cyclobutyl)propane-1-sulfonamide mesylate.
Figure 12:
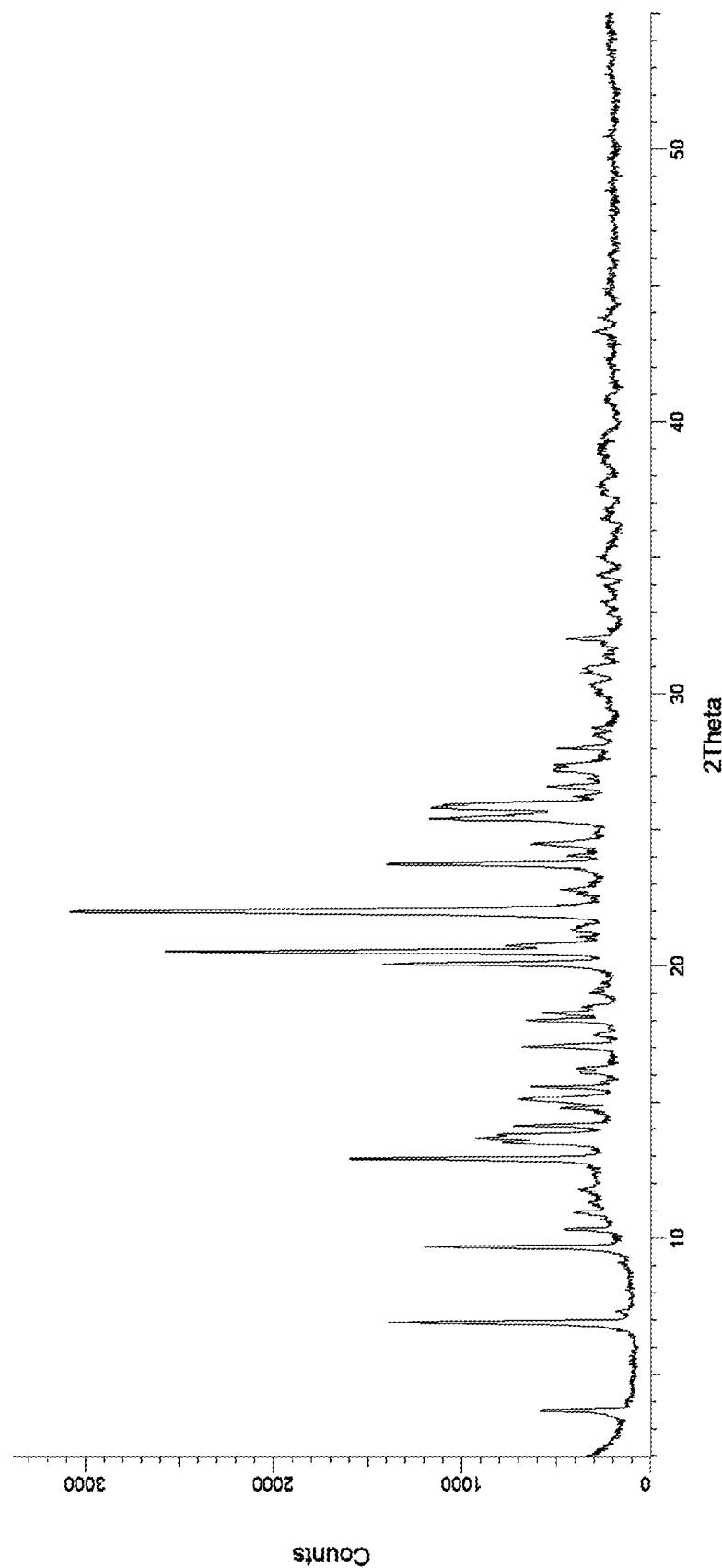
FIG. 12 depicts a powder X-ray diffraction pattern of the crystalline form of N-((1S,3S)-3-(methyl(7H-pyrrolo[2,3-d]pyrimidin-4-yl)amino)cyclobutyl)propane-1-sulfonamide p-tosylate.
Figure 13:
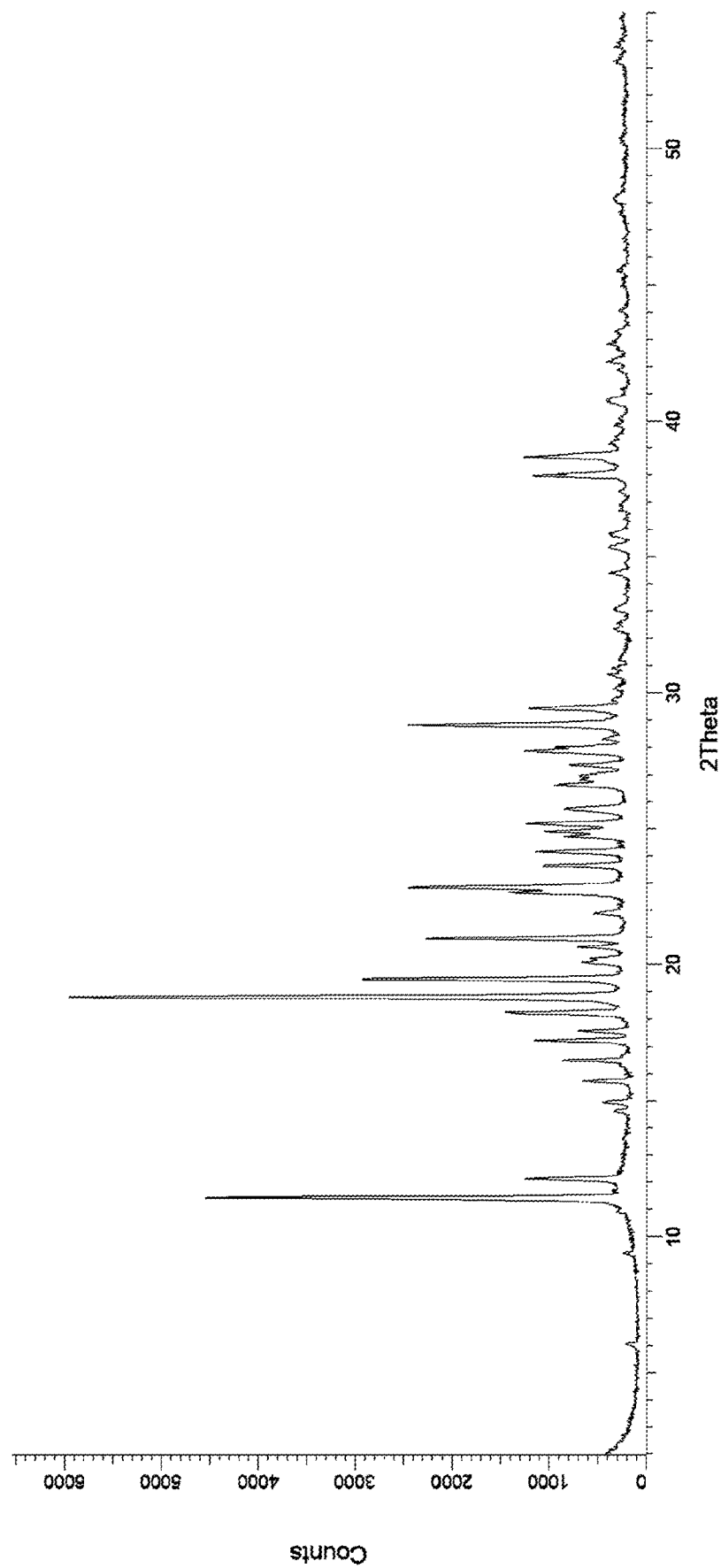
FIG. 13 depicts a powder X-ray diffraction pattern of the crystalline form of N-((1S,3S)-3-(methyl(7H-pyrrolo[2,3-d]pyrimidin-4-yl)amino)cyclobutyl)propane-1-sulfonamide hemifumaric acid co-crystal.

The present invention provides a compound useful in the manufacture of N-((1S,3S)-3-(methyl(7H-pyrrolo[2,3-d]pyrimidin-4-yl)amino)cyclobutyl)propane-1-sulfonamide having the structure:

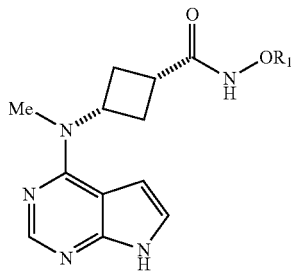

wherein $R_1$ is selected from: hydrogen, substituted or unsubstituted phenyl, substituted or unsubstituted pyridyl, substituted or unsubstituted imidazolyl, $(C_1-C_6)$alkyl, $(C_3-C_{10})$cycloalkyl, which may optionally be substituted with 1, 2 or 3 groups independently selected from halo, $(C_1-C_3)$alkyl, and $(C_1-C_3)$alkyloxy, or a salt thereof selected from a group consisting of sodium, potassium, lithium, magnesium and calcium. In a particular aspect, the invention provides the compound wherein $R_1$ is hydrogen, or a salt thereof.

The present invention also provides a compound (1s,3s)-N-hydroxy-3-(methyl(7H-pyrrolo[2,3-d]pyrimidin-4-yl)amino)cyclobutane-1-carboxamide having the structure:

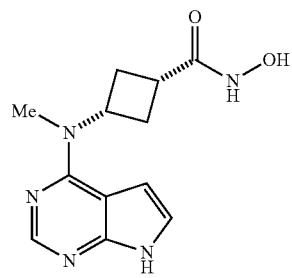

or a salt thereof.

The present invention further provides a compound having the structure:

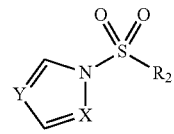

wherein $R_2$ is selected from $(C_3-C_5)$alkyl and $(C_3-C_4)$cycloalkyl; and, X and Y are independently selected from $CR_3$ and N, wherein $R_3$ is selected from: hydrogen, and $(C_1-C_6)$alkyl. In certain aspects, the invention provides the compound wherein X and Y are both N; and, $R_2$ is $(C_3-C_5)$alkyl. In certain other aspects, the invention provides the compound wherein $R_2$ is a linear or branched chain propyl group. In yet certain other aspects, the invention provides the compound wherein $R_2$ is linear propyl group. In certain other aspects, the invention provides the compound wherein X is $CR_3$, wherein $R_3$ is hydrogen; and, Y is N, and further, wherein $R_2$ is a linear or branched chain propyl group. In a particular aspect, the invention provides the compound wherein $R_2$ is linear propyl group. Accordingly, the invention provides the compound 1-(propylsulfonyl)-1H-1,2,4-triazole having the structure:

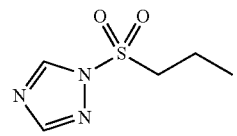

The present invention further provides a salt of a compound having the structure:

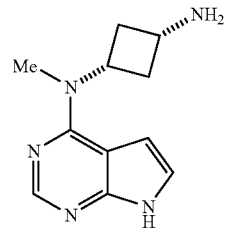

said salt selected from the group consisting of the hydrochloric acid salt, phosphoric (mono, bis, tris) acid salt, (1S)-(+)-10-camphor sulfonic acid salt, 1,2-ethanedisulfonic acid salt, dibenzoyl-L-tartaric acid salt, dibenzoyl-D-tartaric acid salt, citric acid salt, succinic acid salt, fumaric acid salt, maleic acid salt, oxalic acid salt, p-toluenesulfonic acid salt, L-(+)-tartaric acid salt, D-(−)-tartaric acid salt, hydrobromic acid salt, acid salt, mesylate salt and malonic acid salt. In a particular aspect, the present invention provides the phosphoric acid salt of the compound.

The present invention also provides an acid salt of a compound having the structure:

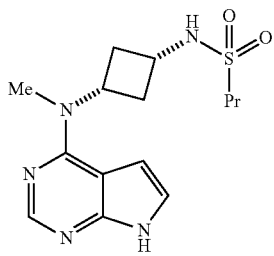

wherein said acid salt is selected from the group consisting of a hydrochloride salt, a phosphate salt, a succinic acid salt, a citrate salt, a p-toluenesulfonic acid salt, a mesylate salt, a hemisulfate salt, a hemifumarate salt and a malonic acid salt. In a certain aspect, the present invention provides an acid salt of a compound having the structure:

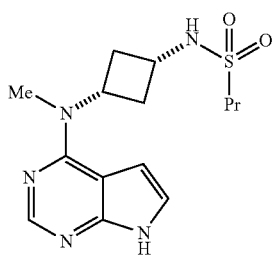

wherein the acid salt is a hydrochloride salt.

The present invention further provides a compound having the structure:

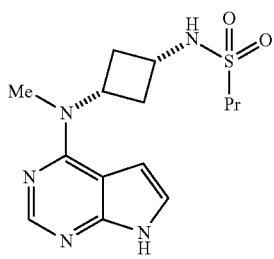

prepared from an acid salt selected from the group consisting of a hydrochloride salt, a phosphate salt, a succinic acid salt, a p-toluenesulfonic acid salt, a mesylate salt, a hemisulfate salt, a citrate salt, a hemifumarate salt and a malonic acid salt. In a particular aspect, the present invention provides the compound prepared from the hydrochloride salt of said compound under suitable basic conditions. More particularly, the present invention provides the compound, having a powder X-ray diffraction pattern comprising peaks, in terms of 2θ, at 13.0°, 14.8° and 23.3° 2θ±0.2° 2θ.

The invention also provides a compound having the structure:

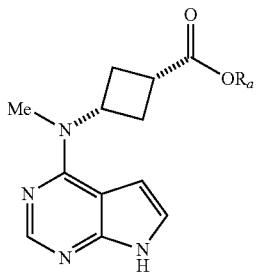

wherein $R_a$ is selected from hydrogen, $(C_1\text{-}C_6)$alkyl, $(C_3\text{-}C_{10})$cycloalkyl, and substituted or unsubstituted phenyl, where said alkyl and cycloalkyl may optionally be substituted with 1, 2 or 3 groups independently selected from halo, $(C_1\text{-}C_3)$alkyl, and $(C_1\text{-}C_3)$alkyloxy, or a salt thereof. In a particular aspect, the invention provides the above compound wherein $R_a$ is hydrogen. In another particular aspect, the invention provides the above compound wherein $R_a$ is methyl or isopropyl.

In addition, the present invention provides a process for preparing a compound having the structure:

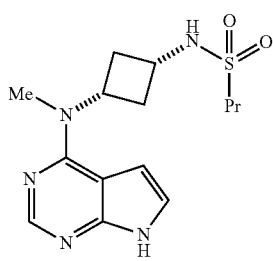

which comprises (a) preparing the hydrochloric acid salt of said compound under suitable conditions, and thereafter (b) reacting said salt with a suitable base under suitable conditions to form the compound, wherein said suitable base is selected from sodium carbonate, potassium carbonate, sodium bicarbonate, potassium bicarbonate, sodium hydroxide, potassium hydroxide, or triethylamine. In a certain aspect, the present invention provides the process, wherein said suitable base is sodium or potassium bicarbonate.

The present invention also provides a process for preparing a compound having the structure:

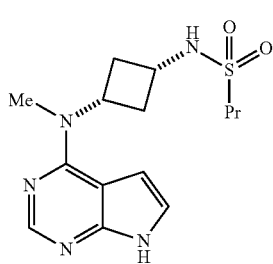

which comprises (a) preparing a hydroxylamine compound having the structure:

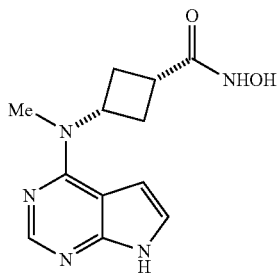

(b) reacting said hydroxylamine compound under suitable conditions to prepare an amino compound having the structure:

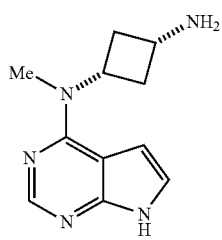

and thereafter (c) treating said amino compound with a suitable n-propylsulfonation reagent under suitable conditions to form the compound. In certain aspects, the present invention provides the process, wherein the n-propylsulfonation reagent is a compound having the structure:

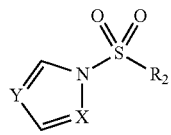

wherein $R_2$ is n-propyl; and, X and Y are independently selected from $CR_3$ and N, wherein $R_3$ is selected from: hydrogen, and ($C_1$-$C_6$)alkyl. In particular aspects, the present invention provides the process, wherein X and Y are both N. In other aspects, the present invention further provides the process, wherein the n-propylsulfonation reagent is a compound 1-(propylsulfonyl)-1H-1,2,4-triazole having the structure:

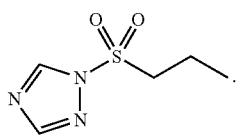

In yet another aspect, the present invention provides the process wherein the compound having the structure:

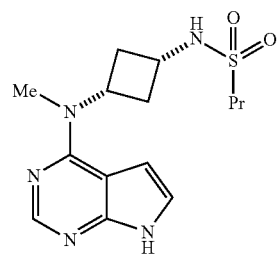

is a crystalline form of N-((1S,3S)-3-(methyl(7H-pyrrolo[2,3-d]pyrimidin-4-yl)amino)cyclobutyl)propane-1-sulfonamide, having a powder X-ray diffraction pattern comprising peaks, in terms of 2θ, at 13.0°, 14.8° and 23.3° 2θ±0.2° 2θ.

The present invention additionally provides a process for preparing a compound having the structure:

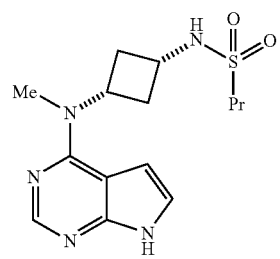

which comprises (a) preparing an amino compound having the structure:

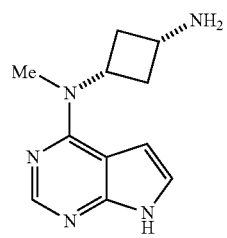

and thereafter (b) treating said amino compound with a suitable n-propylsulfonation reagent under suitable conditions to form the compound. In certain aspects, the present invention provides the process, wherein the n-propylsulfonation reagent is a compound having the structure:

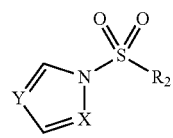

wherein $R_2$ is n-propyl; and, X and Y are independently selected from $CR_3$ and N, wherein $R_3$ is selected from hydrogen and ($C_1$-$C_6$)alkyl. In certain aspects, the present invention provides the process, wherein X and Y are both N.

In other certain aspects, the present invention provides the process, wherein the n-propylsulfonation reagent is a compound 1-(propylsulfonyl)-1H-1,2,4-triazole having the structure:

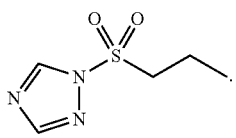

The present invention further provides the process wherein the compound having the structure:

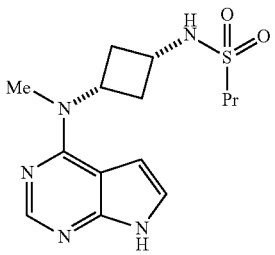

is a crystalline form of N-((1S,3S)-3-(methyl(7H-pyrrolo[2,3-d]pyrimidin-4-yl)amino)cyclobutyl)propane-1-sulfonamide, having a powder X-ray diffraction pattern comprising peaks, in terms of 2θ, at 13.0°, 14.8° and 23.3° 2θ±0.2° 2θ.

In addition, the present invention provides a pharmaceutical composition of a compound having the structure:

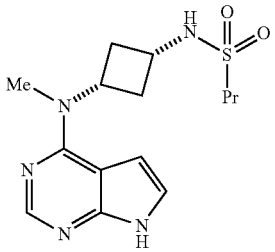

wherein said composition is prepared from said compound having a crystalline form having a powder X-ray diffraction pattern comprising peaks, in terms of 2θ, at 13.0°, 14.8° and 23.3° 2θ±0.2° 2θ; and further comprises a pharmaceutically acceptable carrier. In certain aspects, the present invention provides a pharmaceutical composition, comprising a topical formulation selected from a cream, transdermal patch, ointment, ophthalmic drops, lotion and gel. In particular, the present invention provides the pharmaceutical composition wherein the topical formulation contains from about 0.1% to about 5.0% (w/v)N-((1S,3S)-3-(methyl(7H-pyrrolo[2,3-d]pyrimidin-4-yl)amino)cyclobutyl)propane-1-sulfonamide.

The present invention further provides a method of treating a disease in a mammal, comprising administering to a mammal in need thereof a therapeutically effective amount of a pharmaceutical composition disclosed hereinabove, wherein the disease is selected from the group consisting of lupus, rheumatoid arthritis, IBD, ulcerative colitis, Crohn's Disease, vitiligo, alopecia, psoriasis and atopic dermatitis.

The present invention also provides a method of topically treating a disease in a mammal, comprising administering by a topical mode of administration to a mammal in need thereof a therapeutically effective amount of a pharmaceutical composition disclosed hereinabove, wherein the disease is selected from the group consisting of vitiligo, alopecia, psoriasis and atopic dermatitis.

The present invention further provides a pharmaceutical composition disclosed hereinabove for use as a medicament.

The present invention additionally provides a pharmaceutical composition disclosed hereinabove for use in the treatment of a disorder selected from the group consisting of lupus, rheumatoid arthritis, IBD, ulcerative colitis, Crohn's Disease, vitiligo, alopecia, psoriasis and atopic dermatitis.

The present invention also provides for the use of the pharmaceutical composition disclosed hereinabove for the preparation of a medicament for the treatment of a disorder selected from the group consisting of lupus, rheumatoid arthritis, IBD, ulcerative colitis, Crohn's Disease, vitiligo, alopecia, psoriasis and atopic dermatitis.

Instrument and Analysis Methods:

Calculated Powder Patterns:

Powder patterns were calculated from single crystal X-ray data using the SHELXTL package of programs, including XFOG (SHELXTL, Bruker AXS, XFOG, Version 5.100, 1997) and XPOW (SHELXTL, Bruker AXS, XPOW, Version 5.102, 1997-2000). The appropriate wavelength needed for overlay graphics was added using the XCH file exchange program (SHELXTL, Bruker AXS, XCH, Version 5.0.4, 1995-2001).

Powder X-Ray Diffraction:

Powder X-ray diffraction analysis was conducted using a Bruker AXS D8 Advance diffractometer equipped with a Cu radiation source, equipped with a twin primary utilizing a gobel mirror. Diffracted radiation was detected by a LYNX-EYE_EX detector with motorized slits. Both primary and secondary equipped with 2.5 soller slits. The X-ray tube voltage and amperage were set at 40 kV and 40 mA respectively. Data was collected in the Theta-Theta goniometer in a locked couple scan at Cu K-alpha wavelength from 3.0 to 40.0 degrees 2-Theta with 1204 steps using a scan speed of 0.50 seconds per step. Samples were prepared by placement in a silicon low background sample holder and rotated during collection. Data were collected using Bruker DI FFRAC Plus software. Analysis performed by EVA diffract plus software. The PXRD data file was not processed prior to peak searching. Using the peak search algorithm in the EVA software, peaks selected with a threshold value of 1 were used to make preliminary peak assignments. To ensure validity, adjustments were manually made; the output of automated assignments was visually checked and peak positions were adjusted to the peak maximum. Peaks with relative intensity of 2% were generally chosen. The peaks which were not resolved or were consistent with noise were not selected. A typical error associated with the peak position from PXRD stated in USP up to +1-0.2° 2-Theta (USP-941).

PXRD Reflection Assignments:

Eva Application 9.0 software was used to visualize and evaluate PXRD spectra. Peak values were assigned at the maximum intensity of a given reflection. All reflections exhibiting a relative intensity of greater than 10% are included within the following tables.

The present invention provides a pharmaceutical composition prepared from a crystalline form of N-((1S,3S)-3-(methyl(7H-pyrrolo[2,3-d]pyrimidin-4-yl)amino)-cyclobutyl)propane-1-sulfonamide which can be identified by one or more solid state analytical methods.

PXRD peak list for the crystalline form at 23° C. is shown in Table 1.

TABLE 1

PXRD peak list for Form 1. Peak positions represent of characteristic peaks of N-((1S,3S)-3-(methyl(7H-pyrrolo[2,3-d]pyrimidin-4-yl)amino)cyclobut-yl)propane-1-sulfonamide, Form 1 anhydrous free base.

| Angle (2 theta) | Relative Intensity (%) | Angle (2 theta) | Relative Intensity (%) |
|---|---|---|---|
| 12.6 | 6 | 24.3 | 4 |
| 13.0* | 34 | 25.0 | 21 |
| 13.4 | 2 | 25.4 | 13 |
| 14.8* | 100 | 26.0 | 7 |
| 15.9 | 2 | 26.5 | 2 |
| 16.6 | 2 | 26.9 | 3 |
| 17.6* | 9 | 27.3 | 3 |
| 18.0* | 14 | 29.9 | 2 |
| 18.6 | 4 | 30.3 | 2 |
| 19.5* | 13 | 31.9 | 2 |
| 20.3 | 8 | 32.5 | 2 |
| 20.6* | 11 | 34.9 | 2 |
| 21.6 | 4 | 35.3 | 2 |
| 22.3 | 2 | 37.5 | 2 |
| 23.1 | 6 | 37.7 | 2 |
| 23.3* | 34 | 39.5 | 2 | b) Defined as peak heights. Intensities can vary depending on the actual setup of the CPMAS experimental parameters and the thermal history of the sample. CPMAS intensities are not necessarily quantitative.
*Peak shoulder Accordingly, the present invention provides pharmaceutical compositions prepared from a crystalline form, and to methods for preparing such forms, as well as pharmaceutical compositions for use in medicine and for use in treating such diseases as lupus, rheumatoid arthritis, IBD, ulcerative colitis, Crohn's Disease, vitiligo, alopecia, psoriasis and atopic dermatitis. The present invention also provides the use of such pharmaceutical compositions in the manufacture of a medicament for treating such diseases as lupus, rheumatoid arthritis, IBD, ulcerative colitis, Crohn's Disease, vitiligo, alopecia, psoriasis and atopic dermatitis.

Methods of treating the diseases and syndromes listed herein are understood to involve administering to an individual in need of such treatment a therapeutically effective amount of a pharmaceutical composition of the polymorph prepared in accord with the process of the invention. As used herein, the term "treating" in reference to a disease is meant to refer to preventing, inhibiting and/or ameliorating the disease.

As used herein, the term "individual" or "patient," used interchangeably, refers to any animal, including mammals, preferably mice, rats, other rodents, rabbits, dogs, cats, swine, cattle, sheep, goats, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) preventing the disease; for example, preventing a disease, condition or disorder in an individual that may be predisposed to the disease, condition or disorder but does not yet experience or display the pathology or symptomatology of the disease;

(2) inhibiting the disease; for example, inhibiting a disease, condition or disorder in an individual that is experiencing or displaying the pathology or symptomatology of the disease, condition or disorder (i.e., arresting or slowing further development of the pathology and/or symptomatology); and (3) ameliorating the disease; for example, ameliorating a disease, condition or disorder in an individual that is experiencing or displaying the pathology or symptomatology of the disease, condition or disorder (i.e., reversing the pathology and/or symptomatology).

Dosage and Formulation

The invention also includes pharmaceutical compositions as described herein including one or more pharmaceutically acceptable carriers, excipients, vehicles, etc.

The pharmaceutical composition of the invention is administered in an amount effective to treat a condition as described herein and can be prepared from the crystalline compound per se, or alternatively, as a pharmaceutically acceptable salt thereof.

The pharmaceutical composition of the invention is administered by any suitable route in the form of a composition adapted to such a route, and in a dose effective for the treatment intended. The compounds of the invention may be administered orally, rectally, vaginally, parenterally, or topically.

The pharmaceutical composition of the invention may be administered orally. Oral administration may involve swallowing, so that the compound enters the gastrointestinal tract, or buccal or sublingual administration may be employed by which the compound enters the bloodstream directly from the mouth.

In another embodiment, the pharmaceutical composition of the invention may also be administered directly into the bloodstream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the pharmaceutical composition of the invention may also be administered topically to the skin or mucosa, that is, dermally or transdermally. In another embodiment, the pharmaceutical composition of the invention can also be administered intranasally or by inhalation. In another embodiment, the compounds of the invention may be administered rectally or vaginally. In another embodiment, the pharmaceutical composition of the invention may also be administered directly to the eye or ear.

The dosage regimen for the pharmaceutical compositions of the invention is based on a variety of factors, including the type, age, weight, sex and medical condition of the patient; the severity of the condition; the route of administration; and the activity of the particular compound employed. Thus, the dosage regimen may vary widely. In one embodiment, the total daily dose of a compound is typically from about 0.01 to about 100 mg/kg (i.e., mg compound of the invention per kg body weight) for the treatment of the indicated conditions discussed herein. In another embodiment, total daily dose of the compound is from about 0.1 to about 50 mg/kg, and in another embodiment, from about 0.5 to about 30 mg/kg.

For oral administration, the compositions may be provided in the form of tablets containing 0.01, 0.05, 0.1, 0.5, 1.0, 2.5, 5.0, 10.0, 15.0, 25.0, 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.01 to about 10 mg/kg/minute during a constant rate infusion.

Suitable subjects according to the invention include mammalian subjects. Mammals according to the invention include canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises pharmaceutical compositions containing a compound along with a pharmaceutically acceptable carrier. Other pharmacologically active substances can also be present. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof, and may include isotonic agents, for example, sugars, sodium chloride, or polyalcohols such as mannitol, or sorbitol in the composition. Pharmaceutically acceptable substances such as wetting agents or minor amounts of auxiliary substances such as wetting or emulsifying agents, preservatives or buffers, which enhance the shelf life or effectiveness of the antibody or antibody portion.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form depends on the intended mode of administration and therapeutic application.

Typical compositions are in the form of injectable or infusible solutions, such as compositions similar to those used for passive immunization of humans with antibodies in general. One mode of administration is parenteral (e.g. intravenous, subcutaneous, intraperitoneal, or intramuscular). In another embodiment, the antibody is administered by intravenous infusion or injection. In yet another embodiment, the antibody is administered by intramuscular or subcutaneous injection.

Oral administration of a solid dose form may be, for example, presented in discrete units, such as hard or soft capsules, pills, cachets, lozenges, or tablets, each containing a predetermined amount of at least one compound recited herein. In another embodiment, the oral administration may be in a powder or granule form. In another embodiment, the oral dose form is sub-lingual, such as, for example, a lozenge. In such solid dosage forms, the crystalline compound is ordinarily combined with one or more adjuvants. Such capsules or tablets may contain a controlled release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the invention comprises a parenteral dose form. "Parenteral administration" includes, for example, subcutaneous injections, intravenous injections, intraperitoneally, intramuscular injections, intrasternal injections, and infusion. Injectable preparations (i.e., sterile injectable aqueous or oleaginous suspensions) may be formulated according to the known art using suitable dispersing, wetting agents, and/or suspending agents.

In another embodiment, the invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a crystalline compound which enhances absorption or penetration of the active ingredient through the skin or other affected areas. When the crystalline compound of this invention is administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, B. C. Finnin and T. M. Morgan, J. Pharm. Sci., vol. 88, pp. 955-958, 1999.

Accordingly, topical formulations prepared from the crystalline or noncrystalline form of N-((1S,3S)-3-(methyl(7H-pyrrolo[2,3-d]pyrimidin-4-yl)amino)cyclobutyl)propane-1-sulfonamide in accord with the process of the invention may be administered using such preparations encompassing all conventional methods of administration across the surface of the body and the inner linings of body passages including epithelial and mucosal tissues, including transdermal, epidermal, buccal, pulmonary, ophthalmic, intranasal, vaginal and rectal modes of administration. Typical carriers include alcohol, water, mineral oil, liquid petrolatum, white petrolatum, glycerin, polyethylene glycol and propylene glycol. Such topical formulations may be prepared in combination with additional pharmaceutically acceptable excipients. An excipient which may be essential to clinical efficacy is one or more penetration enhancer such as be one or more saturated or cis-unsaturated C10-C18 fatty alcohols. Such fatty alcohols include C16-C18 fatty alcohols, and most preferably, are a C18 fatty alcohol. Examples of cis-unsaturated C16-C18 fatty alcohols include oleyl alcohol, linoleyl alcohol, γ-linolenyl alcohol and linolenyl alcohol. Saturated C10-C18 fatty alcohols useful as penetration enhancers include decyl alcohol, lauryl alcohol, myristyl alcohol, cetyl alcohol and stearyl alcohol. Alternatively, other penetration enhancers which may be used to prepare the topical formulations include C10-C18 fatty acids, which when saturated may include capric acid, lauric acid, myristic acid, palmitic acid, stearic acid and arachidic acid. Alternatively, the penetration enhancer may usefully be a cis-unsaturated fatty acid, such as palmitoleic acid (cis-9-hexadecenoic acid), oleic acid (cis-9-octadecenoic acid), cis-vaccenic acid (cis-11-octadecenoic acid), linoleic acid (cis-9,12-octadecadienoic acid), γ-linolenic acid (cis-6,9,12-octadecatrienoic acid), linolenic acid (cis-9,12,15-octadecatrienoic acid) and arachidonic acid (cis-5,8,11,14-eicosatetraenoic acid). The penetration enhancers, for example, one selected from C10-C18 fatty alcohols, are used in amounts ranging from about 0.1 to about 5% (w/v), more preferably, from 1 to about 4%, more preferably still, 1 to about 3% (w/v).

Topical formulations contain N-((1S,3S)-3-(methyl(7H-pyrrolo[2,3-d]pyrimidin-4-yl)amino)cyclobutyl)propane-1-sulfonamide in therapeutically effective amounts that can be given in daily or twice daily doses to patients in need. These amounts range from about 0.1% to about 5.0% (w/v), more preferably, from about 0.1% to about 3.0% (w/v). Among other excipients which enhance the stability of these formulations include aldehyde scavengers, such as glycerine and propylene glycol, and antioxidants, such as butyl hydroxyanisole (BHA), butyl hydroxytoluene (BHT), propyl gallate, ascorbic acid (Vitamin C), polyphenols, tocopherols (Vitamin E), and their derivatives.

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (i.e., absorbable gel sponges, collagen) and non-biodegradable (i.e., silicone) implants, wafers, lenses and particulate or vesicular systems, such as niosomes or liposomes. A polymer such as crossed linked polyacrylic acid, polyvinyl alcohol, hyaluronic acid, a cellulosic polymer, for example, hydroxypropylmethylcellulose, hydroxyethylcellulose, or methylcellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the crystalline compound of the invention is conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the invention comprises a rectal dose form prepared from the crystalline or noncrystalline form of N-((1S,3S)-3-(methyl(7H-pyrrolo[2,3-d]pyrimidin-4-yl)amino)cyclobutyl)propane-1-sulfonamide in accord with the process of the invention. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients (3rd Ed.), American Pharmaceutical Association, Washington, 1999.

The crystalline or noncrystalline form of N-((1S,3S)-3-(methyl(7H-pyrrolo[2,3-d]pyrimidin-4-yl)amino)cyclobutyl)propane-1-sulfonamide in accord with the process of the invention can be used alone, or in combination with other therapeutic agents. The invention provides any of the uses, methods or compositions as defined herein wherein the crystalline or noncrystalline form herein, or pharmaceutically acceptable solvate of said compound, is used in combination with one or more other therapeutic agent discussed herein.

The administration of two or more compounds "in combination" means that all of the compounds are administered closely enough in time that the presence of one alters the biological effects of any other compound(s). The two or more compounds may be administered simultaneously, concurrently or sequentially. Additionally, simultaneous administration may be carried out by mixing the compounds prior to administration or by administering the compounds at the same point in time but as separate dosage forms at the same or different site of administration.

The phrases "concurrent administration," "co-administration," "simultaneous administration," and "administered simultaneously" mean that the compounds are administered in combination.

In another embodiment, the invention provides methods of treatment that include administering the crystalline or noncrystalline form of N-((1S,3S)-3-(methyl(7H-pyrrolo[2,3-d]pyrimidin-4-yl)amino)cyclobutyl)propane-1-sulfonamide in accord with the process of the invention in combination with one or more other pharmaceutical agents, wherein the one or more other pharmaceutical agents may be selected from the agents discussed herein.

These agents and the crystalline or noncrystalline form of N-((1S,3S)-3-(methyl(7H-pyrrolo[2,3-d]pyrimidin-4-yl)amino)cyclobutyl)propane-1-sulfonam-ide in accord with the process of the invention can be combined with pharmaceutically acceptable vehicles such as saline, Ringer's solution, dextrose solution, and the like. The particular dosage regimen, i.e., dose, timing and repetition, will depend on the particular individual and that individual's medical history.

Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or Igs; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Liposomes containing these agents and/or compounds of the invention are prepared by methods known in the art, such as described in U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

These agents and/or the crystalline or noncrystalline form of N-((1S,3S)-3-(methyl(7H-pyrrolo[2,3-d]pyrimidin-4-yl)amino)cyclobutyl)propane-1-sulfonamide in accord with the process of the invention may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy, 20th Ed., Mack Publishing (2000).

Sustained-release preparations may be used. Suitable examples of sustained-release preparations include semipermeable matrices of solid hydrophobic polymers containing the antibody/compound of the invention, which matrices are in the form of shaped articles, e.g., films, or microcapsules. Examples of sustained-release matrices include polyesters, hydrogels (for example, poly(2-hydroxyethyl-methacrylate), or 'poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as those used in LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for intravenous administration must be sterile. This is readily accomplished by, for example, filtration through sterile filtration membranes. The crystalline or noncrystalline form of N-((1S,3S)-3-(methyl(7H-pyrrolo[2,3-d]pyrimidin-4-yl)amino)cyclobutyl)propane-1-sulfonam-ide in accord with the process of the invention is generally placed into a container having a sterile access port, for example, an intravenous solution bag or vial having a stopper pierceable by a hypodermic injection needle.

Suitable emulsions may be prepared using commercially available fat emulsions, such as Infralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 μm, particularly 0.1 and 0.5 μm, and have a pH in the range of 5.5 to 8.0.

The reagents used in the preparation of the crystalline or noncrystalline form of N-((1S,3S)-3-(methyl(7H-pyrrolo[2,3-d]pyrimidin-4-yl)amino)cyclobutyl)propane-1-sulfonamide in accord with the process of the invention of these teachings can be either commercially obtained or can be prepared by standard procedures described in the literature. For example, the crystalline or noncrystalline form of the present invention can be prepared according to the methods illustrated in the following examples.

The description of this invention utilizes a variety of abbreviations well known to those skilled in the art, including the following:
aq.: aqueous
$CH_3CN$: Acetonitrile
DCM: Dichloromethane
DMF: N,N-Dimethylformamide
DMSO: Dimethylsulfoxide
EtOAc: Ethyl acetate
EtOH: Ethanol
FT-IR: Fourier Transform-Infrared
HOAc: Acetic acid
MeOH: Methanol
PXRD: powder X-ray diffraction
ss $^{13}$C NMR: solid state $^{13}$C nuclear magnetic resonance
THF: Tetrahydrofuran
TLC: Thin Layer Chromatography

EXAMPLES

The following non-limiting example is presented merely to illustrate the present invention. The skilled person will understand that there are numerous equivalents and variations not exemplified but which still form part of the present teachings.

Example 1

Preparation of N-((1S,3S)-3-(methyl(7H-pyrrolo[2,3-d]pyrimidin-4-yl)amino)-cyclobutyl)propane-1-sulfonamide Form I The Title compound is prepared according to Example 2 of U.S. Pat. No. 9,035,074. The crude material is warmed in 10 vol (100 mg/ml) 2:1 EtOH/water to 80° C. (until entirely dissolved), and then passed through a polishing filtration, and slowly cooled until the product crystallises. After filtration, the material is dried under vacuum at 45-55° C.

Example 2

Alternative Preparation of N-((1S,3S)-3-(methyl(7H-pyrrolo[2,3-d]pyrimidin-4-yl)amino)cyclobutyl)propane-1-sulfonamide Isopropyl 3-oxocyclobutane-1-carboxylate (A)

The commercially available 3-cyclobutanone carboxylic acid (175 g) was dissolved in 2-propanol (1050 mL) and p-toluenesulfonic acid monohydrate was added (11.85 g, 4 mol %). The solution was heated to 80° C. and stirred for 19 hours. The reaction was deemed complete by UPLCMS and cooled. The reaction was concentrated to a light yellow oil and diluted with 1000 mL of MTBE. The solution was washed with 300 mL of saturated sodium bicarbonate and separated. The aqueous layer was discarded and washed with an additional 200 mL of saturated sodium bicarbonate. The layers were separated, and the aqueous layer discarded. The MTBE layer was dried with 200 mL of brine and then magnesium sulfate. The MTBE solution was then concentrated to a pale yellow oil. $^1$H NMR (400 MHz, DMSO-d$_6$) δ 4.95 (hept, J=6.3 Hz, 1H), 3.38-3.18 (m, 5H), 1.22 (d, J=6.3 Hz, 6H).

Isopropyl (1s,3s)-3-(methylamino)cyclobutane-1-carboxylate (Free Base) (B)

An aqueous solution of methyl amine (75 mL, 40 wt %) was charged to a reactor followed by phosphate buffer (700 mL, pH 7.2, 100 mM) composed of mono- and dipotassium phosphate. The pH of the solution was adjusted to 8.8 by slow addition of concentrated hydrochloric acid. NADP+ (700 mg), GDH (350 mg), and glucose (150 g) were then added. The IRED enzyme (50 mL lysate) was charged to the reactor. The isopropyl 3-oxocyclobutane-1-carboxylate ester substrate (100 g) was diluted with DMSO (25 mL) and charged. The reaction was warmed to 30° C. and the pH maintained at 7.5 by use of a pH probe and dosing unit (2N sodium hydroxide). The reaction was monitored by GC and UPLC analysis. When the reaction was deemed complete, the mixture was filtered through Celite™ (50 g) and the Celite™ cake washed with water (100 mL). The aqueous solution was added to a separatory funnel and MTBE (500 mL) was charged and shaken. The MTBE layer was separated and discarded. The aqueous layer was then basified with sodium hydroxide (50% aqueous solution) to a pH of 12. MTBE (1 L) was then added and the funnel shaken. The phases were split, and the MTBE collected and set aside. The aqueous layer was extracted once more with additional MTBE (700 mL) and the layers split. The aqueous was discarded and the MTBE solutions were each filtered over additional Celite™ (36.5 g). The MTBE solutions were then combined and dried over anhydrous sodium sulphate. $^1$H NMR (400 MHz, DMSO-d$_6$) δ 4.86 (hept, J=6.3 Hz, 1H), 2.96 (tt, J=8.7, 7.0 Hz, 1H), 2.67 (tt, J=9.7, 8.1 Hz, 1H), 2.41-2.26 (m, 2H), 2.15 (s, 3H), 1.78 (dtd, J=9.8, 8.8, 2.6 Hz, 2H), 1.17 (d, J=6.2 Hz, 6H).

Isopropyl (1s,3s)-3-(methylamino)cyclobutane-1-carboxylate (Succinate Salt) (B Succinate)

The crude biocatalytic reaction (1125 mL) was concentrated to approximately half volume (530 mL). A separate reactor was charged with succinic acid (75.6 g) and 2MeTHF (1100 mL) and heated to 60° C. to dissolve the acid. The solution was cooled to 50° C. and the approximately half the amine solution was added. The resulting turbid solution was held for 30 minutes and was a thin slurry. The rest of the amine solution was then charged in. The solution was cooled to 20° C. and then warmed up to 50° C. resulting in a slurry. The slurry was held for 30 minutes at 50° C. and then cooled to 20° C. and stirred overnight. The slurry was filtered and washed with two portions of 2-MeTHF (100 mL each) and the material dried in an oven. 95.7 g isolated (52% yield). $^1$H NMR (400 MHz, DMSO-d$_6$) δ 4.88 (hept, J=6.2 Hz, 1H), 3.30 (tt, J=8.8, 7.3 Hz, 1H), 2.82 (tt, J=9.8, 8.2 Hz, 1H), 2.43-2.34 (m, 2H), 2.31 (d, J=2.5 Hz, 7H), 2.13-2.00 (m, 2H), 1.18 (d, J=6.3 Hz, 6H).

Isopropyl (1s,3s)-3-(methylamino)cyclobutane-1-carboxylate (B HCl Salt)

The crude amine (8 g) was dissolved in MTBE (80 mL) and heated to 50 C. Hydrochloric acid in dioxane was then added (11 mL, 4M). A stirrable slurry was observed and the reaction held at 50° C. for 1 hour. The slurry was cooled to 20 C and then filtered and washed with two portions of MTBE (20 mL each). The material was then dried under vacuum. 8.7 g isolated (96% yield). $^1$H NMR (400 MHz, DMSO-d6) δ 9.26 (s, 2H), 4.89 (hept, J=6.3 Hz, 1H), 3.52 (tt, J=9.0, 7.5 Hz, 1H), 2.92 (tt, J=9.8, 8.2 Hz, 1H), 2.45-2.35 (m, 5H), 2.34-2.24 (m, 2H), 1.18 (d, J=6.3 Hz, 6H).

Isopropyl (1s,3s)-3-(methyl(7H-pyrrolo[2,3-d]pyrimidin-4-yl)amino)cyclo-butane-1-carboxylate (C; CSNAr)

The succinate salt of the amine (B succinate, 75.4 g) and the chloropyrrolopyrimdine (40.0 g) were combined in a reactor. 2-Propanol (200 mL) was charged resulting in a slurry. Diisopropylethylamine (114 mL) was charged resulting in a thin slurry. The reaction was heated to 80° C. which resulted in a solution. The reaction was held at 80° C. until the reaction was deemed complete by UPLCMS (approximately 48 hours). The reaction was cooled to 20° C. and became a slurry. The solids were filtered and washed with two portions of 2-propanol (80 mL each). 61 g of material isolated (81%). $^1$H NMR (400 MHz, DMSO-d6) δ 11.64 (s, 1H), 8.11 (s, 1H), 7.16 (dd, J=3.6, 2.4 Hz, 1H), 6.62 (dd, J=3.6, 1.9 Hz, 1H), 5.24 (tt, J=9.4, 8.0 Hz, 1H), 4.91 (hept, J=6.3 Hz, 1H), 3.25 (s, 3H), 2.87 (tt, J=9.2, 8.0 Hz, 1H), 2.48-2.35 (m, 4H), 1.20 (d, J=6.3 Hz, 6H).

(1s,3s)-N-Hydroxy-3-(methyl(7H-pyrrolo[2,3-d]pyrimidin-4-yl)amino)cyclo-butane-1-carboxamide (D; Hydroxamic Amide)

To a reactor was charged methanol (500 mL) and sodium methoxide in methanol (93.7 mL, 25 mass %) under nitrogen. Hydroxylamine hydrochloride (15.1 g) was charged to the room temperature reaction resulting in a slight endotherm. Iso-propyl (1s,3S)-3-(methyl(7H-pyrrolo[2,3-d]pyrimidin-4-yl)amino)cyclobut-ane-1-carboxylate (C; 50 g) was then added resulting in a white slurry. The reaction was warmed to 40° C. and stirred overnight and deemed complete by UPLCMS. The thick slurry was then charged with hydrochloric acid (1M) until a pH of 7.0 is achieved. The slurry is then filtered and rinsed with methanol (100 mL). The material was dried in a vacuum oven overnight resulting in 42.7 g of white solids (94% yield). $^1$H NMR (400 MHz, DMSO-d6) δ 11.63 (s, 1H), 10.46 (s, 1H), 8.75 (s, 1H), 8.10 (s, 1H), 7.15 (dd, J=3.6, 1.9 Hz, 1H), 6.61 (dd, J=3.7, 1.4 Hz, 1H), 5.21 (p, J=9.6 Hz, 1H), 3.28 (s, 3H), 2.60 (p, J=8.3 Hz, 1H), 2.49-2.37 (m, 2H), 2.35-2.26 (m, 2H).

(1s,3s)-N1-Methyl-N1-(7H-pyrrolo[2,3-d]pyrimidin-4-yl)cyclobutane-1,3-diamine (E; Phosphate Salt)

Hydroxamic amide D (19.4 g) was charged to a reactor followed by 2-MeTHF (388 mL) resulting in a white slurry. The slurry was warmed to 30° C. and carbonyl diimidazole (16.1 g) was added. The reaction was stirred overnight. The reaction was deemed complete by UPLCMS. A solution of phosphoric acid (14.7 M in water, 25.5 mL) was diluted with water (78 mL) was prepared and added slowly to the slurry. The slurry dissolved and the reaction was heated to 60° C. and held for several hours. The reaction was deemed complete and sodium hydroxide (20 mass % in water, 16.4 m) was added to obtain a pH of approximately 6. The reaction was then warmed to 80° C. and then cooled to 25° C. 2-Propanol (58 mL) was added slowly and the solids filtered.

The cake was washed with 2-propanol/water (1:1, 40 mL) and dried in a vacuum oven resulting in 19.1 g (81% yield). $^1$H NMR (600 MHz, Deuterium Oxide, 35° C.) δ 8.08 (s, 1H), 7.20 (d, J=3.6 Hz, 1H), 6.66 (d, J=3.6 Hz, 1H), 4.81 (tt, J=9.6, 7.4 Hz, 1H), 3.67 (tt, J=8.9, 7.3 Hz, 1H), 3.28 (s, 3H), 2.96-2.73 (m, 2H), 2.47 (qd, J=9.4, 2.9 Hz, 2H). $^{31}$P NMR (243 MHz, Deuterium Oxide, 35 C) δ 0.31.

(1s,3s)-N$^1$-Methyl-N$^1$-(7H-pyrrolo[2,3-d]pyrimidin-4-yl)cyclobutane-1,3-diamine (Free Amine)

Amino phosphate E (10 g) was dissolved in H$_2$O (30 mL). Hydrochloric acid (6N) was added until the pH was 2, resulting in a clear solution. The pH was raised to 12 using sodium hydroxide (50 wt %) resulting in a thick suspension. The slurry was purified using reverse-phase chromatography (10:90 CH$_3$CN:H$_2$O 2CV, gradient to 40:60 CH$_3$CN:H$_2$O over 4CV). The appropriate fractions were collected, combined, and concentrated in vacuo, affording the amine freebase E as a white solid (6.05 g, 88% yield). $^1$H NMR (400 MHz, Deuterium Oxide) δ 7.78 (s, 1H), 6.91 (d, J=3.6 Hz, 1H), 6.24 (d, J=3.6 Hz, 1H), 4.25 (ddd, J=9.7, 7.4, 2.3 Hz, 1H), 3.08 (td, J=7.9, 7.1, 1.8 Hz, 1H), 2.95 (s, 3H), 2.58-2.39 (m, 2H), 1.86 (dd, J=9.4, 2.8 Hz, 2H).

1-(Propylsulfonyl)-1H-1,2,4-triazole (Triazole Reagent)

1,2,4-Triazole (11.98 g) and THF (40 mL) were charged to a reactor equipped with overhead stirring. The suspension was stirred for 10 minutes, then 1-propanesulfonyl chloride (7.89 mL, 68.0 mmol) was added at 20° C. The resulting slurry was stirred at 20° C. until the starting material was consumed as judged by $^1$H NMR. Once complete, the reaction was filtered, and the filtrate transferred to a separatory funnel where it was diluted with water (20 mL) and extracted with dichloromethane (50 mL). The layers were separated, and the DCM layer was washed with water (2×20 mL) and brine (1×20 mL). The organic layer was dried with MgSO$_4$, filtered, and concentrated in vacuo, affording the sulfonyl triazole as a viscous, clear colorless oil (10.66 g, 89% yield). $^1$H NMR (400 MHz, Chloroform-d) δ 8.67 (s, 1H), 8.13 (s, 1H), 3.55-3.46 (m, 2H), 1.76 (h, J=7.5 Hz, 2H), 1.03 (t, J=7.5 Hz, 3H).

Example 3

Alternate Preparation of N-((1S,3S)-3-(methyl(7H-pyrrolo[2,3-d]pyrimidin-4-yl)-amino)cyclobutyl) propane-1-sulfonamide Sulfonylation Using Triazole Reagent 1-(Propylsulfonyl)-1H-1,2,4-triazole Water (18 mL) and the amine phosphate salt E (3 g) were charged to a reactor followed by sodium hydroxide in water (19M, 1.5 mL). The reaction exothermed slightly and was cooled to 25° C. 1-(Propylsulfonyl)-1H-1,2,4-triazole (4.3 g) was dissolved in THF (12 mL) and added to the hydroxide reaction. Once the reaction was deemed complete, water (18 mL) was added and the material was filtered and dried. 2.57 g (84% yield) was obtained.

In-Situ Preparation of Reagent

The lithium salt of 1,2,4-triazole (1.0 g) and THF (8 mL) was charged to a reactor at 20° C. The 1-propanesulfonyl chloride (1.47 mL) was then charged. The slurry was stirred at 20° C. until the sulfonyl chloride has been consumed as judged by H NMR. In a separate flask, the amino-phosphate (2.0 g) was dissolved in H$_2$O (12 mL) at 20° C., and then sodium hydroxide (1.0 mL, 50 wt %) was added keeping the temperature below 30° C. The aqueous solution was cooled to 10° C., then the THF solution of the 1-propanesulfonyl-triazole reagent was added maintaining the temperature below 20° C. The resulting suspension was stirred until <5% of the amine is remaining according to UPCLMS, then sodium hydroxide (0.67 mL, 50 wt %) was added and the reaction heated to 50° C. Once the sulfonyl triazole reagent was consumed by UPLC, the reaction was cooled to 20° C., and the pH adjusted to 5-6 using hydrochloric acid (6N). The resulting slurry was cooled to 10° C. and held for 30 minutes and filtered. The cake was rinsed with 75:25 H$_2$O:THF (10 mL), and the solids dried at 50° C. in a vacuum oven, affording the desired product as an off-white solid.

Sulfonylation Using 1-propanesulfonyl Chloride

Amine phosphate salt E (3.07 g) was charged to a reactor followed by water (18 mL). Sodium hydroxide (2.9 mL, 10M) was then added to the slurry and the mixture stirred at room temperature. 2-MeTHF (12 mL) was added and the mixture cooled to 10 C. The 1-propanesulfonyl chloride (1.6 mL) was added resulting in an exotherm. The reaction was monitored and deemed complete. Water (18 mL) was then added and the slurry granulated at 10° C. The slurry was filtered, washed with water (5 mL), and dried under vacuum. 3.0 g of pale yellow solid were isolated (96% yield).

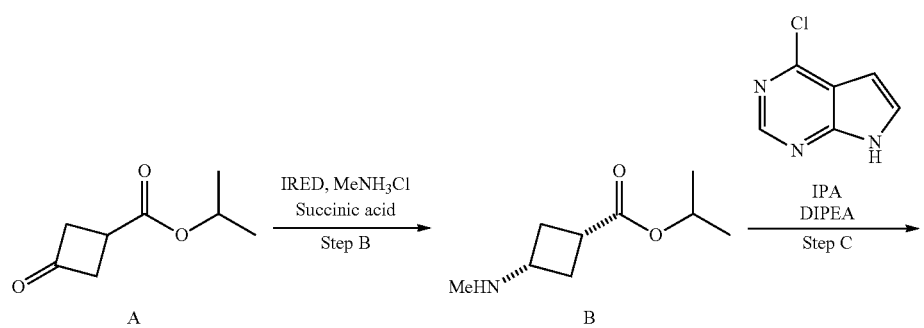

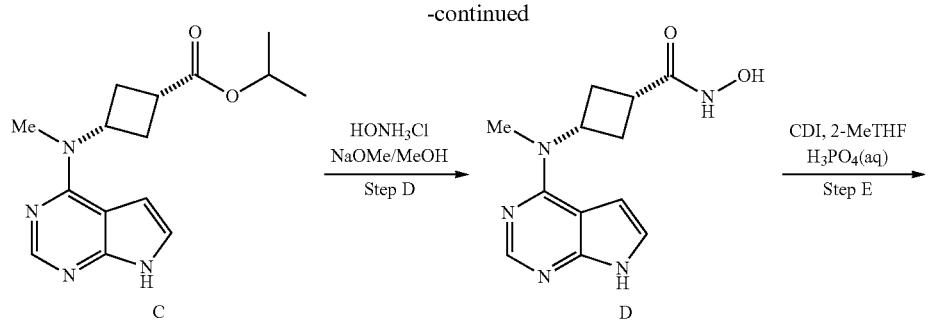
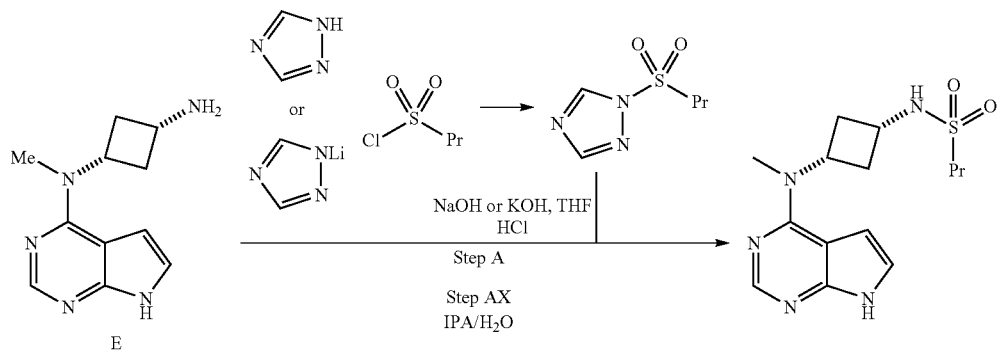
Example 4
Alternative Preparation of (1s,3s)-$N^1$-Methyl-$N^1$-(7H-pyrrolo[2,3-d]pyrimidin-4-yl)cyclobutane-1,3-diamine
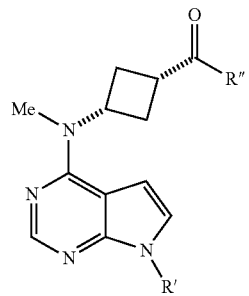
R″ = OH, NH$_2$, NHOH
R′ = H, other group (tosyl, etc)
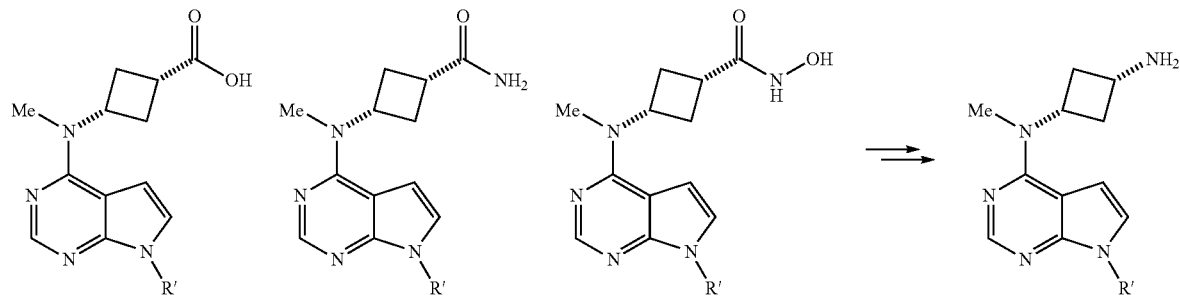

Preparation of (1s,3s)-3-(methyl-(7-tosyl-7H-pyrrolo[2,3-d]pyrimidin-4-yl)amino)cyclobutane-1-carboxamide

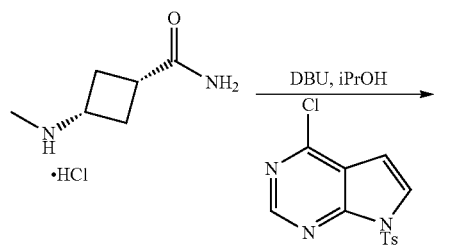

To a 20 mL Schlenk tube, charge the amino-amide hydrochloride (500 mg, 3.04 mmol 1.0 equiv) and isopropanol (4 mL), followed by the chloro-pyrrolopyrimidine (1.03 g, 3.34 mmol, 1.1 equiv) and DBU (0.97 g, 6.38 mmol, 2.1 equiv). Heat the resulting mixture to 85° C., and stir until the reaction is complete by UPLC. Once complete, cool the mixture to 40° C., at which point water (20 mL) is added, resulting in a clear solution. Continue cooling to 20° C., resulting is solids precipitating from the reaction. Filter the solids and rinse the filter cake with H$_2$O (30 mL). The crude solids (1.18 g) were purified by reverse-phase chromatography (gradient 4:6 MeOH:H$_2$O to 100% MeOH, 20 CV). The desired fractions were combined, and the methanol removed in vacuo, resulting in solids precipitating. The solids were filtered, rinsed with H$_2$O (10 mL), and dried in a vacuum oven at 50° C., affording the desired S$_N$Ar product as a white solid (686 mg, 57% yield). $^1$H NMR (400 MHz, DMSO-d$_6$) δ 8.24 (s, 1H), 7.97 (d, J=8.4 Hz, 2H), 7.63 (d, J=4.1 Hz, 1H), 7.43 (d, J=8.6 Hz, 2H), 7.31 (s, 1H), 6.96 (d, J=4.1 Hz, 1H), 6.82 (s, 1H), 5.07 (p, J=8.6 Hz, 1H), 3.22 (s, 3H), 2.70 (p, J=8.6 Hz, 1H), 2.40-2.26 (m, 7H). $^{13}$C NMR (101 MHz, DMSO-d$_6$) δ 175.6, 157.1, 152.8, 151.7, 146.2, 134.9, 130.4, 128.2, 122.0, 106.9, 104.8, 47.3, 32.2, 31.7, 31.0, 21.6.

Preparation of (1s,3s)-3-(methyl(7H-pyrrolo[2,3-d]pyrimidin-4-yl)amino)cyclobutane-1-carboxylic Acid

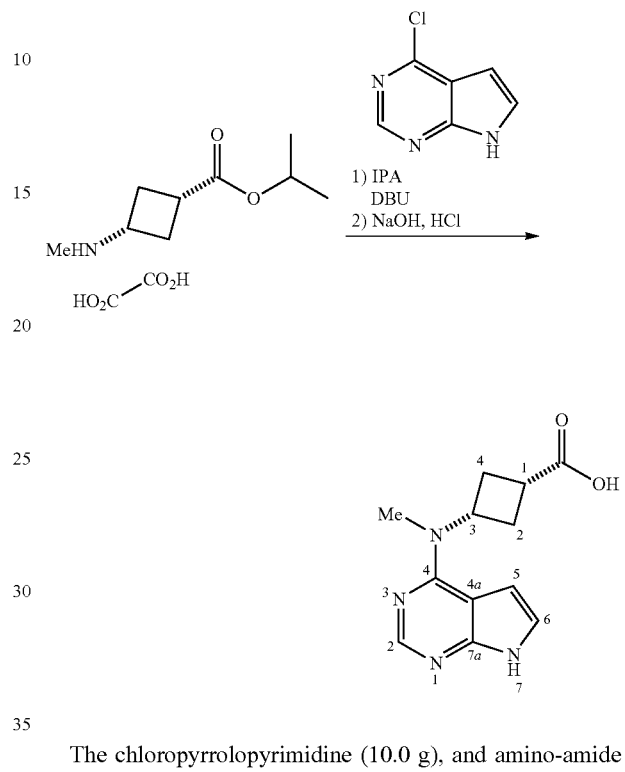

The chloropyrrolopyrimidine (10.0 g), and amino-amide oxalate salt (18.7 g) were charged to a reactor. IPA (100 mL) was added and the slurry stirred. DBU (39 mL) was added and the mixture heated to 80° C. Once the reaction was deemed complete, water and sodium hydroxide were added, and the reaction stirred at 80° C. until it became a thick slurry. IPA (60 mL) was added and the slurry was stirred and filtered. 26.39 g of the acid-DBU adduct was isolated. 10.0 g of the DBU adduct was dissolved in water (125 mL) at 45° C. Hydrochloric acid (4 mL, 6M) was added and the resulting precipitate was stirred and filtered. The solids were washed with water (10 mL). The solids were dried (2.47 g). $^1$H NMR (400 MHz, DMSO-d$_6$) δ 2.44 (d, J=8.8 Hz, 4H), 2.44 (d, J=8.8 Hz, 4H), 2.77-2.91 (m, 1H), 3.26 (s, 3H), 3.31-3.41 (m, 1H), 5.23 (t, J=8.7 Hz, 1H), 6.54-6.72 (m, 1H), 7.08-7.26 (m, 1H), 8.12 (s, 1H), 11.65 (br s, 1H), 12.13-12.43 (m, 1H).

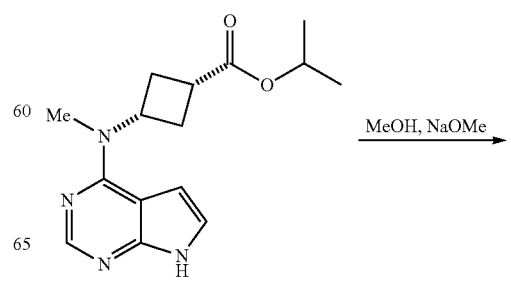

27

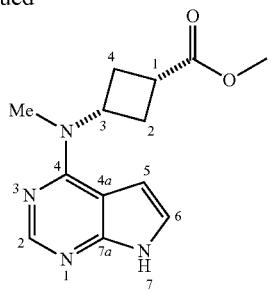

Preparation of Methyl (1s,3s)-3-(methyl(7H-pyrrolo[2,3-d]pyrimidin-4-yl)amino)cyclobutane-1-carboxylate The isopropyl ester isopropyl (1s,3S)-3-(methyl(7H-pyrrolo[2,3-d]pyrimidin-4-yl)amino)cyclobutane-1-carboxylate, 15.03 g) was charged to a reactor with methanol (75 ml) and stirred at 25° C. Sodium methoxide (25 mass % in methanol, 15 mL) was added dropwise and the reaction stirred until deemed complete by UPLCMS. The solids were filtered, washed with methanol (20 mL), and dried in a vacuum oven to yield 11.27 g of white solids. $^1$H NMR (400 MHz, Chloroform-d) δ 11.48 (s, 1H), 8.33 (s, 1H), 7.09 (d, J=3.6 Hz, 1H), 6.58 (d, J=3.6 Hz, 1H), 5.58-5.23 (m, 1H), 3.72 (s, 3H), 3.39 (s, 3H), 2.88 (dq, J=10.0, 8.1 Hz, 1H), 2.69-2.52 (m, 4H). $^{13}$C NMR (101 MHz, CDCl$_3$) δ 175.36, 157.64, 152.11, 150.87, 120.46, 103.41, 102.02, 52.06, 47.38, 32.03, 31.80, 31.20.

Example 5

General Procedure for Salt Formation for Compound E:

Compound E was dissolved in various solvents listed in Table 2 then added up to 4 equivalents of counterions/coformers listed in Table 3. All samples were temperature cycled and solids were isolated for characterization.

TABLE 2

| No. | Solvents |
|---|---|
| 1 | Water |
| 2 | MeOH |
| 3 | MeCN |
| 4 | THF |
| 5 | IPA |
| 6 | Acetone |
| 7 | EtOAc |
| 8 | DCM |
| 9 | MTBE |
| 10 | Toluene |
| 11 | MIBK |
| 12 | 1,4-Dioxane |

TABLE 3

| No. | Counterions/Coformers |
|---|---|
| 1 | Hydrochloric acid |
| 2 | Sulfuric acid |
| 3 | p-Toluenesulfonic acid |
| 4 | Benzenesulfonic acid |
| 5 | Phosphoric acid |
| 6 | Malonic acid |

28

TABLE 3-continued

| No. | Counterions/Coformers |
|---|---|
| 7 | L-Tartaric acid |
| 8 | L-Malic acid |
| 9 | Succinic acid |
| 10 | Acetic acid |
| 11 | Methanesulfonic acid |
| 12 | Hydrobromic acid |
| 13 | L-Pyroglutamic acid |
| 14 | Nicotinic acid |
| 15 | Nicotinamide |
| 16 | Resorcinol |
| 17 | 3-Hydroxybenzoic acid |
| 18 | 4-Hydroxybenzoic acid |

Example 6

Alternate Preparation of N-((1S,3S)-3-(methyl(7H-pyrrolo[2,3-d]pyrimidin-4-yl)amino)cyclobutyl)propane-1-sulfonamide from Aminocyclobutane

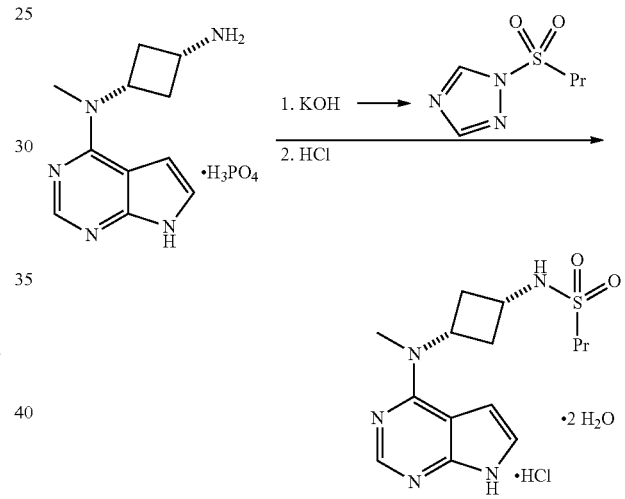

Preparation of Sulfonyl Triazole:

In a 250 mL flask, charge water (75 mL) and 1,2,4-triazole (37.24 g, 1.7 equiv), and stir until dissolved. Once the solution is homogenous, transfer it to a 2 L vessel containing THF (400 mL) and equipped with overhead stirring. Warm the solution to 35° C., then charge anhydrous LiOH powder (13.18 g, 1.7 equiv). Stir the resulting suspension for 30 minutes, or until all solids have dissolved. Once homogenous, add 1-propanesulfonyl chloride (58.84 mL, 1.6 equiv) slowly, keeping the internal temperature below 40° C. Once addition is complete, continue stirring the solution at 35° C. for 30 minutes, then cool to 0° C. and hold until the free-basing of amine phosphate salt E is complete.

Formation of Free Base E from Phosphate Salt E:

In a 1 L vessel equipped with overhead stirring, charge water (300 mL) and THF (200 mL), followed by aq. 11.5M KOH (82.75 mL, 3.0 equiv) and warm to 25° C. Charge amine phosphate salt E (100 g, 1.0 equiv) in 5 portions, and continue stirring until all solids have dissolved. Stop agitation and allow phases to separate. Discard aqueous (bottom) phase. Continue stirring the organic phase while cooling to 8° C.

Primary Procedure:

Charge the cooled amine (free base) solution to the sulfonyl triazole solution, maintaining the internal temperature below 10° C. Rinse the amine containing vessel with a minimal amount of THF, if necessary. Once the transfer is complete, warm the resulting solution to 20° C. at 1° C./min. Stir for 90 minutes, then charge aq. 11.5 M KOH (13.8 mL, 0.5 equiv). Continue stirring until <5% of amine E remains. When complete, add water (1.14 L) followed by aq. 11.5M KOH (110.3 mL, 4 equiv). Heat the mixture to 40° C. and hold for 4 hours, then cool to 10° C. Once cool, begin vacuum distillation (100 mbar), warming slowly to an internal temperature of 45-50° C., at which point the final solution volume is between 1.65-1.70 L, indicating the distillation is complete. Cool the mixture to 40° C., then add conc. HCl (149 mL, 5.7 equiv), targeting a pH between 2.0-3.0, maintaining an internal temperature between 40-45° C. Warm the mixture to 65° C., hold for 15 minutes, then cool at 0.5°/min to 53° C. Once reached, charge N-((1S,3S)-3-(methyl(7H-pyrrolo[2,3-d]pyrimidin-4-yl)amino)-cyclobutyl)propane-1-sulfonamide HCl seed (500 mg, 0.005 g/g). Cool to 50° C. and stir for 30 minutes, followed by cooling to 10° C. at a rate of 0.1° C./min. Stir at 10° C. for 1 hour, then filter through a 600 mL coarse fritted Buchner funnel. Rinse the filter cake with $H_2O$ chilled to 10° C. (200 mL). Dry the solids on the funnel, targeting a final water content of 9.5% by Karl Fisher titration. $^1$H NMR (400 MHz, DMSO-$d_6$) δ 12.81 (s, 1H), 8.34 (s, 1H), 7.64 (d, J=9.3 Hz, 1H), 7.52-7.43 (m, 1H), 7.00 (dd, J=3.7, 1.8 Hz, 1H), 4.75 (t, J=8.3 Hz, 1H), 3.63 (h, J=8.4 Hz, 1H), 3.00-2.90 (m, 2H), 2.73 (dtd, J=10.0, 7.4, 2.9 Hz, 2H), 2.35 (qd, J=9.1, 2.7 Hz, 2H), 1.68 (h, J=7.5 Hz, 2H), 0.98 (t, J=7.4 Hz, 3H). $^{13}$C NMR (101 MHz, DMSO-$d_6$) δ 152.2, 146.3, 143.2, 124.5, 105.0, 102.2, 54.2, 47.2, 41.3, 36.6, 34.0, 17.3, 13.2.

N-((1S,3S)-3-(Methyl(7H-pyrrolo[2,3-d]pyrimidin-4-yl)amino)cyclobutyl)propane-1-sulfonamide N-((1S,3S)-3-(Methyl(7H-pyrrolo[2,3-d]pyrimidin-4-yl)amino)cyclobutyl)propane-1-sulfonamide HCl (8 g) was charged to a reactor followed by isopropanol (56 mL) and water (20 mL). The mixture was heated to 60° C. A solution of potassium bicarbonate (2.4 g) in water (8 mL) was prepared and added to the heated mixture. The mixture was heated to 80° C., then cooled to 65° C. Seed crystals of the title compound (70 mg) were charged. The reactor was then cooled to 20° C. and then milled. The material was vacuum-filtered and washed with two 2/1 isopropanol/water washes (14 mL each). The cake was dried under vacuum to yield 6.09 g (87% yield) of the title compound. $^1$H NMR (400 MHz, DMSO-$d_6$) δ 11.65 (s, 1H), 8.13 (s, 1H), 7.50 (d, J=9.2 Hz, 1H), 7.15 (dd, J=3.6, 1.6 Hz, 1H), 6.63 (d, J=3.5 Hz, 1H), 4.91 (tt, J=9.6, 7.4 Hz, 1H), 3.70-3.47 (m, 1H), 3.26 (s, 3H), 3.04-2.87 (m, 2H), 2.61 (ddd, J=11.7, 8.9, 5.2 Hz, 2H), 2.24 (dt, J=11.8, 9.1 Hz, 2H), 1.79-1.55 (m, 2H), 0.98 (t, J=7.4 Hz, 3H).

Example 7

General Preparation of Salts of N-((1S,3S)-3-(Methyl(7H-pyrrolo[2,3-d]pyrimidin-4-yl)amino)cyclobutyl)propane-1-sulfonamide N-((1S,3S)-3-(Methyl(7H-pyrrolo[2,3-d]pyrimidin-4-yl)amino)cyclobutyl)propane-1-sulfonamide was dissolved in acetone, ethanol, isopropanol, water, or blends thereof. An amount of the acid (hydrochloric acid, methanesulfonic acid, p-toluenesulfonic acid, fumaric acid or sulfuric acid) was added and the samples were temperature cycled. Solids were isolated for characterization.

Example 8

Biotransformation of Isopropyl 3-oxocyclobutane-1-carboxylate Ester to Isopropyl (1s,3s)-3-(methylamino) cyclobutane-1-carboxylate with Recombinant Reductive Aminase Enzyme Reductive amination of isopropyl 3-oxocyclobutane-1-carboxylate ester with methyl amine was evaluated with various recombinant reductive aminase (RedAm) and Imine reductase (IRED) enzymes with protein sequences ID 1-15 and point mutants of SEQ ID 3 as per Table 4. Reactions (50 mL) were carried out at 30° C. in potassium phosphate buffer (100 mM, pH 7.0), NADP+ (0.6 mM), GDH (0.5 mg/ml) Glucose (820 mM), methylamine (960 mM), isopropyl 3-oxocyclobutane-1-carboxylate ester (640 mM) and RedAm enzyme (3 wt % of lyophilized CFL) of SEQ ID 1-15. After 48 h, reaction samples (0.05 mL) were quenched with 200 ul of 1 M sodium bicarbonate and diluted with 0.85 mL acetonitrile, centrifuged and analyzed by GC to give the results shown in Table 1 & 2.

```
                                                       SEQ ID 1
MAADSRAPVTVIGLGAMGSALARAFLAAGHPTTVWNRSPDKADDLVGQGAV
RAATVADAMSAGNLIVICVLDYRAMREIIDSTGHSPADRVIVNLTSGTPGD
ARATAAWAQEQGMEYIDGAIMATPSMIGSEETLIFYGGPQEVYDAHADTLR
SIAGAGTYLGEEPGLPSLYDVALLGLMWTTWAGFMHSAALLASEKVPAAAF
LPYAQAWFEYVISPEVPNLATQVDTGAYPDNDSTLGMQTVAIEHLVEASRT
QGVDPTLPEFLHARAEQAIRRGHAGDGFGAVFEVLRAPAAQ
```

```
                                                       SEQ ID 2
MKPTLTVIGAGRMGSALIKAFLQSGYTTTVWNRTKAKSEPLAKLGAHLADT
VRDAVKRSDIIVVNVLDYDTSDQLLRQDEVTRELRGKLLVQLTSGSPALAR
EQETWARQHGIDYLDGAIMATPDFIGQAECALLYSGSAALFEKHRAVLNVL
GGATSHVGEDVGHASALDSALLFQMWGTLFGTLQALAISRAEGIPLEKTTA
FIKLTEPVTQGAVADVLTRVQQNRLTADAQTLASLEAHNVAFQHLLALCEE
RNIHRGVADAMYSVIREAVKAGHGKDDFAILTRFLK
```

```
                                                       SEQ ID 3
MAREKVTVIGLGQMGSALAAAFLDAGHPTTVWNRTPGKADALVERGAVRAE
TVAVAVAASELVVVCVLDYPAVRDLLAPVVAALPGRAVVNLTTGSPEQARE
EAAWAAGHGFAYLDGAVMTTPPGIGDSANMILYSGAPEVLAAHRDALAVLG
DPVDLGADAGLASLYDAGLLGLMWSVFGGWLHATALVGADGVSAKEFTEVA
NRWLRTVSWFMTGYADQIDTGVYPGDDATIDVQVAAIGHLLHAGEDRGIDP
RLPRLHLELMKGAVAAGHGGDSYARLIETFRGR
```

```
                                                       SEQ ID 4
MAREKVTVIGLGRMGSALAAAFLDAGHPTTVWNRTPGKADALVERGAVRAE
TVAVAVAASELVVVCVLDYPAVRDLLAPVVAALPGRAVVNLTTGSPEQARE
EAAWAAGHGFAYLDGAVMTTPPGIGDSANMILYSGAPEVLAAHRDALAVLG
DPVDLGADAGLASLYDAGLLGLMWSVFGGWLHATALVGADGVSAKEFTEVA
NRWLRTVSWFMTGYADQIDTGVYPGDDATIDVQVAAIGHLLHAGEDRGIDP
RLPRLHLELMKGAVAAGHGGDSYARLIETFRGR
```

```
                                                       SEQ ID 5
MAREKVTVIGLGQMGSALAAAFLDAGHPTTVWNRTPGKADALVERGAVRAE
TVAVAVAASELVVVCVLDYPAVRDLLAPVVAALPGRAVVNLTTGSPEQARE
EAAWAAGHGFAYLDGAVMTTPPGIGDSAHMILYSGAPEVLAAHRDALAVLG
DPVDLGADAGLASLYDAGLLGLMWSVFGGWLHATALVGADGVSAKEFTEVA
NRWLRTVSWFMTGYADQIDTGVYPGDDATIDVQVAAIGHLLHAGEDRGIDP
RLPRLHLELMKGAVAAGHGGDSYARLIETFRGR
```

```
                                                       SEQ ID 6
MAREKVTVIGLGQMGSALAAAFLDAGHPTTVWNRTPGKADALVERGAVRAE
TVAVAVAASELVVVCVLDYPAVRDLLAPVVAALPGRAVVNLTTGSPEQARE
EAAWAAGHGFAYLDGAVMTTPPGIGDSANMILYSGAPEVLAAHRDALAVLG
DPVDLGADAGLASLYDMGLLGLMWSVFGGWLHATALVGADGVSAKEFTEVA
NRWLRTVSWFMTGYADQIDTGVYPGDDATIDVQVAAIGHLLHAGEDRGIDP
RLPRLHLELMKGAVAAGHGGDSYARLIETFRGR
```

-continued

SEQ ID 7
MAREKVTVIGLGQMGSALAAAFLDAGHPTTVWNRTPGKADALVERGAVRAE
TVAVAVAASELVVVCVLDYPAVRDLLAPVVAALPGRAVVNLTTGSPEQARE
EAAWAAGHGFAYLDGAVMTTPPGIGDSANMILYSGAPEVLAAHRDALAVLG
DPVDLGADAGLASLYDAGLLGLMWSVMGGWLHATALVGADGVSAKEFTEVA
NRWLRTVSWFMTGYADQIDTGVYPGDDATIDVQVAAIGHLLHAGEDRGIDP
RLPRLHLELMKGAVAAGHGGDSYARLIETFRGR

SEQ ID 8
MAREKVTVIGLGRMGSALAAAFLDAGHPTTVWNRTPGKADALVERGAVRAE
TVAVAVAASELVVVCVLDYPAVRDLLAPVVAALPGRAVVNLTTGSPEQARE
EAAWAAGHGFAYLDGAVMTTPPGIGDSANMILYSGAPEVLAAHRDALAVLG
DPVDLGADAGLASLYDAGLLGLMWSVFGGWLHATALVGADGVSAKEFTEVA
NRWLRTVSWIMTGYADQIDTGVYPGDDATIDVQVAAIGHLLHAGEDRGIDP
RLPRLHLELMKGAVAAGHGGDSYARLIETFRGR

SEQ ID 9
MAREKVTVIGLGRMGSALAAAFLDAGHPTTVWNRTPGKADALVERGAVRAE
TVAVAVAASELVVVCVLDYPAVRDLLAPVVAALPGRAVVNLTTGSPEQARE
EAAWAAGHGFAYLDGAVMTTPPGIGDSANMILYSGAPEVLAAHRDALAVLG
DPVDLGADAGLASLYDMGLLGLMWSVFGGWLHATALVGADGVSAKEFTEVA
NRWLRTVSWFMTGYADQIDTGVYPGDDATIDVQVAAIGHLLHAGEDRGIDP
RLPRLHLELMKGAVAAGHGGDSYARLIETFRGR

SEQ ID 10
MAREKVTVIGLGRMGSALAAAFLDAGHPTTVWNRTPGKADALVERGAVRAE
TVAVAVAASELVVVCVLDYPAVRDLLAPVVAALPGRAVVNLTTGSPEQARE
EAAWAAGHGFAYLDGAVMTTPPGIGDSANMILYSGAPEVLAAHRDALAVLG
DPVDLGADAGLASLYDAGLLGLMWSVFGGWLHATALVGADGVSAKEFTEVA
NRWLRTVSWIMTGYADQIDTGVYPGDDATIDVQVAAIGHLLHAGEDRGIDP
RLPRLHLELMKGAVAAGHGGDSYARLIETFRGR

SEQ ID 11
MAREKVTVIGLGQMGSALAAAFLDAGHPTTVWNRTPGKADALVERGAVRAE
TVAVAVAASELVVVCVLDYPAVRDLLAPVVAALPGRAVVNLTTGSPEQARE
EAAWAAGHGFAYLDGAVMTTPPGIGDSAHMILYSGAPEVLAAHRDALAVLG
DPVDLGADAGLASLYDCGLLGLMWSVMGGWLHATALVGADGVSAKEFTEVA
NRWLRTVSWFMTGYADQIDTGVYPGDDATIDVQVAAIGHLLHAGEDRGIDP
RLPRLHLELMKGAVAAGHGGDSYARLIETFRGR

SEQ ID 12
MAREKVTVIGLGRMGSALAAAFLDAGHPTTVWNRTPGKADALVERGAVRAE
TVAVAVAASELVVVCVLDYPAVRDLLAPVVAALPGRAVVNLTTGSPEQARE
EAAWAAGHGFAYLDGAVMTTPPGIGDSAHMILYSGAPEVLAAHRDALAVLG
DPVDLGADAGLASLYDCGLLGLMWSVFGGWLHATALVGADGVSAKEFTEVA
NRWLRTVSWNMTGYADQIDTGVYPGDDATIDVQVAAIGHLLHAGEDRGIDP
RLPRLHLELMKGAVAAGHGGDSYARLIETFRGR

SEQ ID 13
MAREKVTVIGLGRMGSALAAAFLDAGHPTTVWNRTPGKADALVERGAVRAE
TVAVAVAASELVVVCVLDYPAVRDLLAPVVAALPGRAVVNLTTGSPEQARE
EAAWAAGHGFAYLDGAVMTTPPGIGDSAHMILYSGAPEVLAAHRDALAVLG
DPVDLGADAGLASLYDCGLLGLMWSVMGGWLHATALVGADGVSAKEFTEVA
NRWLRTVSWFMTGYADQIDTGVYPGDDATIDVQVAAIGHLLHAGEDRGIDP
RLPRLHLELMKGAVAAGHGGDSYARLIETFRGR

SEQ ID 14
MAREKVTVIGLGQMGSALAAAFLDAGHPTTVWNRTPGKADALVERGAVRAE
TVAVAVAASELVVVCVLDYPAVRDLLAPVVAALPGRAVVNLTTGSPEQARE
EAAWAAGHGFAYLDGAVMTTPPGIGDSAHMILYSGAPEVLAAHRDALAVLG
DPVDLGADAGLASLYDCGLLGLMWSVMGGWLHATALVGADGVSAKEFTEVA
NRWLRTVSWFMTDYADQIDTGVYPGDDATIDVQVAAIGHLLHAGEDRGIDP
RLPRLHLELMKGAVAAGHGGDSYARLIETFRGR

SEQ ID 15
MAREKVTVIGLGRMGSALAAAFLDAGHPTTVWNRTPGKADALVERGAVRAE
TVAVAVAASELVVVCVLDYPAVRDLLAPVVAALPGRAVVNLTTGSPEQARE
EAAWAAGHGFAYLDGAVMTTPPGIGDSAHMILYSGAPEVLAAHRDALAVLG
DPVDLGADAGLASLYDCGLLGLMWSVMGGWLHATALVGADGVSAKEFTEVA
NRWLRTVSWNMTGYARQIDTGVYPGDDATIDVQVAAIGHLLHAGEDRGIDP
RLPRLHLELMKGAVAAGHGGDSYARLIETFRGR

TABLE 4

List of amino acid residues of RedAm enzyme from *S. purpureus* (SEQ ID 3) identified as hot spots for improved enzyme activity and selectivity compared to wild type enzyme

| | | | | |
|---|---|---|---|---|
| Q13 | E103 | L142 | F180 | Q237 |
| V55 | T122 | V151 | F214 | G242 |
| A93 | I126 | A162 | G217 | D250 |
| S96 | N131 | A170 | D220 | |

Amino acid residues with improved activity and selectivity from table 1 were combined by various techniques to generate next set of variants with 2 of the above-mentioned substitution in each variant and resulted in improved activity over WT and their parents (see Table 5 for results)

TABLE 5

Performance of various recombinant wild type and engineered variants.

| Entry | Sequence ID | % Yield | % de | Accession Number |
|---|---|---|---|---|
| 1* | SEQ ID 1 | 34.66 | 94.4 | 330467367 *Verrucosispora maris* |
| 2* | SEQ ID 2 | 41.95 | 93.6 | 442318762 *Myxococcus stipitatus* |
| 3* | SEQ ID 3 | 27.4 | 99 | 518728468 *Streptomyces purpureus* |
| 4 | SEQ ID 3 | 2.5 | >99 | 518728468 *Streptomyces purpureus* |
| 5 | SEQ ID 4 | 13.2 | >99 | variant |
| 6 | SEQ ID 5 | 6.7 | >99 | variant |
| 7 | SEQ ID 6 | 20.55 | >99 | variant |
| 8 | SEQ ID 7 | 25.88 | >99 | variant |
| 9 | SEQ ID 8 | 18.66 | >99 | variant |
| 10 | SEQ ID 9 | 26.7 | >99 | variant |
| 11 | SEQ ID 10 | 36.56 | >99 | variant |
| 12 | SEQ ID 11 | 85.8 | >99 | variant |
| 13 | SEQ ID 12 | 61.92 | >99 | variant |
| 14 | SEQ ID 13 | 77.23 | >99 | variant |
| 15 | SEQ ID 14 | 90 | >99 | variant |
| 16 | SEQ ID 15 | 66.98 | >99 | variant |

*reaction run with 10x lower substrate loading

Scaleup Example

An aqueous phosphate buffer (pH 7.2, 100 mM, 1.70 L) solution composed of mono- and dipotassium phosphate was charged to a reactor, followed by methyl amine hydrochloride (130 g) and Glucose monohydrate (320 g) and pH adjusted to 7 by slow addition of aqueous sodium hydroxide solution. NADP+ (1.2 g), GDH (0.5 g), and recombinant engineered variant of reductive aminase SEQ ID 3 (5 g) were then added. The isopropyl 3-oxocyclobutane-1-carboxylate ester substrate (200 g) was diluted with DMSO (100 mL) and charged. The reaction was warmed to 30° C. and the pH maintained at 7.5 by use of a pH probe and dosing unit (2N sodium hydroxide). The reaction was monitored by GC and UPLC analysis. When the reaction was deemed complete, the mixture was filtered through Celite™ (100 g) and the Celite™ cake washed with water (200 mL). The aqueous layer was then basified with sodium hydroxide (50% aqueous solution) to a pH of 12. MTBE (2 L) was then added and the funnel shaken. The phases were split, and the MTBE collected and set aside. The aqueous layer was extracted once more with additional MTBE (1 L) and the layers split. The aqueous was discarded and the MTBE solutions were each filtered over additional Celite™ (50 g). The MTBE solutions were then combined and dried over anhydrous sodium sulphate. $^1$H NMR (400 MHz, DMSO-$d_6$) δ 4.86 (hept, J=6.3 Hz, 1H), 2.96 (tt, J=8.7, 7.0 Hz, 1H), 2.67 (tt, J=9.7, 8.1 Hz, 1H), 2.41-2.26 (m, 2H), 2.15 (s, 3H), 1.78 (dtd, J=9.8, 8.8, 2.6 Hz, 2H), 1.17 (d, J=6.2 Hz, 6H).

Isopropyl (1s,3s)-3-(methylamino)cyclobutane-1-carboxylate (Succinate Salt) (B Succinate) 5

The crude biocatalytic reaction (1125 mL) was concentrated to approximately half volume (530 mL). A separate reactor was charged with succinic acid (75.6 g) and 2-MeTHF (1100 mL) and heated to 60° C. to dissolve the acid. The solution was cooled to 50° C. and the approximately half the amine solution was added. The resulting turbid solution was held for 30 minutes and was a thin slurry. The rest of the amine solution was then charged in. The solution was cooled to 20° C. and then warmed up to 50° C. resulting in a slurry. The slurry was held for 30 minutes at 50° C. and then cooled to 20° C. and stirred overnight. The slurry was filtered and washed with two portions of 2-MeTHF (100 mL each) and the material dried in an oven.

95.7 g isolated (52% yield). $^1$H NMR (400 MHz, DMSO-$d_6$) δ 4.88 (hept, J=6.2 Hz, 1H), 3.30 (tt, J=8.8, 7.3 Hz, 1H), 2.82 (tt, J=9.8, 8.2 Hz, 1H), 2.43-2.34 (m, 2H), 2.31 (d, J=2.5 Hz, 7H), 2.13-2.00 (m, 2H), 1.18 (d, J=6.3 Hz, 6H).

Variations, modifications, and other implementations of what is described herein will occur to those skilled in the art without departing from the spirit and the essential characteristics of the present teachings. Accordingly, the scope of the present teachings is to be defined not by the preceding illustrative description but instead by the following claims, and all changes that come within the meaning and range of equivalency of the claims are intended to be embraced therein.

Each of the printed publications, including but not limited to patents, patent applications, books, technical papers, trade publications and journal articles described or referenced in this specification are herein incorporated by reference in their entirety and for all purposes.

We claim:

1. A process for preparing a compound having the structure:

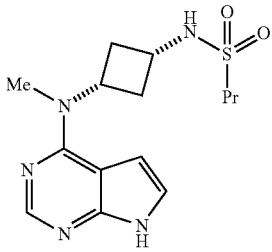

which comprises (a) preparing the hydrochloric acid salt of said compound under suitable conditions, and thereafter (b) reacting said salt with a suitable base under suitable conditions to form the compound, wherein said suitable base is selected from sodium carbonate, potassium carbonate, sodium bicarbonate, potassium bicarbonate, sodium hydroxide, potassium hydroxide, or triethylamine.

2. The process of claim 1, wherein said suitable base is sodium or potassium bicarbonate.

* * * * *

```
                     SEQUENCE LISTING

<160> NUMBER OF SEQ ID NOS: 15

<210> SEQ ID NO 1
<211> LENGTH: 296
<212> TYPE: PRT
<213> ORGANISM: Verrucosispora maris

<400> SEQUENCE: 1

Met Ala Ala Asp Ser Arg Ala Pro Val Thr Val Ile Gly Leu Gly Ala
1               5                   10                  15

Met Gly Ser Ala Leu Ala Arg Ala Phe Leu Ala Ala Gly His Pro Thr
            20                  25                  30

Thr Val Trp Asn Arg Ser Pro Asp Lys Ala Asp Asp Leu Val Gly Gln
        35                  40                  45

Gly Ala Val Arg Ala Ala Thr Val Ala Asp Ala Met Ser Ala Gly Asn
    50                  55                  60

Leu Ile Val Ile Cys Val Leu Asp Tyr Arg Ala Met Arg Glu Ile Ile
65                  70                  75                  80

Asp Ser Thr Gly His Ser Pro Ala Asp Arg Val Ile Val Asn Leu Thr
                85                  90                  95

Ser Gly Thr Pro Gly Asp Ala Arg Ala Thr Ala Ala Trp Ala Gln Glu
            100                 105                 110

Gln Gly Met Glu Tyr Ile Asp Gly Ala Ile Met Ala Thr Pro Ser Met
        115                 120                 125

Ile Gly Ser Glu Glu Thr Leu Ile Phe Tyr Gly Gly Pro Gln Glu Val
    130                 135                 140

Tyr Asp Ala His Ala Asp Thr Leu Arg Ser Ile Ala Gly Ala Gly Thr
145                 150                 155                 160

Tyr Leu Gly Glu Glu Pro Gly Leu Pro Ser Leu Tyr Asp Val Ala Leu
                165                 170                 175

Leu Gly Leu Met Trp Thr Thr Trp Ala Gly Phe Met His Ser Ala Ala
            180                 185                 190

Leu Leu Ala Ser Glu Lys Val Pro Ala Ala Phe Leu Pro Tyr Ala
        195                 200                 205

Gln Ala Trp Phe Glu Tyr Val Ile Ser Pro Glu Val Pro Asn Leu Ala
    210                 215                 220

Thr Gln Val Asp Thr Gly Ala Tyr Pro Asp Asn Asp Ser Thr Leu Gly
225                 230                 235                 240
```

```
Met Gln Thr Val Ala Ile Glu His Leu Val Glu Ala Ser Arg Thr Gln
            245                 250                 255

Gly Val Asp Pro Thr Leu Pro Glu Phe Leu His Ala Arg Ala Glu Gln
            260                 265                 270

Ala Ile Arg Arg Gly His Ala Gly Asp Gly Phe Gly Ala Val Phe Glu
            275                 280                 285

Val Leu Arg Ala Pro Ala Ala Gln
        290                 295

<210> SEQ ID NO 2
<211> LENGTH: 291
<212> TYPE: PRT
<213> ORGANISM: Myxococcus stipitatus

<400> SEQUENCE: 2

Met Lys Pro Thr Leu Thr Val Ile Gly Ala Gly Arg Met Gly Ser Ala
1               5                   10                  15

Leu Ile Lys Ala Phe Leu Gln Ser Gly Tyr Thr Thr Thr Val Trp Asn
            20                  25                  30

Arg Thr Lys Ala Lys Ser Glu Pro Leu Ala Lys Leu Gly Ala His Leu
        35                  40                  45

Ala Asp Thr Val Arg Asp Ala Val Lys Arg Ser Asp Ile Ile Val Val
    50                  55                  60

Asn Val Leu Asp Tyr Asp Thr Ser Asp Gln Leu Leu Arg Gln Asp Glu
65                  70                  75                  80

Val Thr Arg Glu Leu Arg Gly Lys Leu Leu Val Gln Leu Thr Ser Gly
                85                  90                  95

Ser Pro Ala Leu Ala Arg Glu Gln Glu Thr Trp Ala Arg Gln His Gly
            100                 105                 110

Ile Asp Tyr Leu Asp Gly Ala Ile Met Ala Thr Pro Asp Phe Ile Gly
            115                 120                 125

Gln Ala Glu Cys Ala Leu Leu Tyr Ser Gly Ser Ala Ala Leu Phe Glu
        130                 135                 140

Lys His Arg Ala Val Leu Asn Val Leu Gly Gly Ala Thr Ser His Val
145                 150                 155                 160

Gly Glu Asp Val Gly His Ala Ser Ala Leu Asp Ser Ala Leu Leu Phe
                165                 170                 175

Gln Met Trp Gly Thr Leu Phe Gly Thr Leu Gln Ala Leu Ala Ile Ser
            180                 185                 190

Arg Ala Glu Gly Ile Pro Leu Glu Lys Thr Thr Ala Phe Ile Lys Leu
        195                 200                 205

Thr Glu Pro Val Thr Gln Gly Ala Val Ala Asp Val Leu Thr Arg Val
    210                 215                 220

Gln Gln Asn Arg Leu Thr Ala Asp Ala Gln Thr Leu Ala Ser Leu Glu
225                 230                 235                 240

Ala His Asn Val Ala Phe Gln His Leu Leu Ala Leu Cys Glu Glu Arg
                245                 250                 255

Asn Ile His Arg Gly Val Ala Asp Ala Met Tyr Ser Val Ile Arg Glu
            260                 265                 270

Ala Val Lys Ala Gly His Gly Lys Asp Asp Phe Ala Ile Leu Thr Arg
        275                 280                 285

Phe Leu Lys
    290
```

```
<210> SEQ ID NO 3
<211> LENGTH: 288
<212> TYPE: PRT
<213> ORGANISM: Streptomyces purpureus

<400> SEQUENCE: 3

Met Ala Arg Glu Lys Val Thr Val Ile Gly Leu Gly Gln Met Gly Ser
1               5                   10                  15

Ala Leu Ala Ala Ala Phe Leu Asp Ala Gly His Pro Thr Thr Val Trp
            20                  25                  30

Asn Arg Thr Pro Gly Lys Ala Asp Ala Leu Val Glu Arg Gly Ala Val
        35                  40                  45

Arg Ala Glu Thr Val Ala Val Ala Val Ala Ala Ser Glu Leu Val Val
    50                  55                  60

Val Cys Val Leu Asp Tyr Pro Ala Val Arg Asp Leu Leu Ala Pro Val
65                  70                  75                  80

Val Ala Ala Leu Pro Gly Arg Ala Val Val Asn Leu Thr Thr Gly Ser
                85                  90                  95

Pro Glu Gln Ala Arg Glu Ala Ala Trp Ala Ala Gly His Gly Phe
            100                 105                 110

Ala Tyr Leu Asp Gly Ala Val Met Thr Thr Pro Pro Gly Ile Gly Asp
        115                 120                 125

Ser Ala Asn Met Ile Leu Tyr Ser Gly Ala Pro Glu Val Leu Ala Ala
    130                 135                 140

His Arg Asp Ala Leu Ala Val Leu Gly Asp Pro Val Asp Leu Gly Ala
145                 150                 155                 160

Asp Ala Gly Leu Ala Ser Leu Tyr Asp Gly Leu Leu Gly Leu Met
                165                 170                 175

Trp Ser Val Phe Gly Gly Trp Leu His Ala Thr Ala Leu Val Gly Ala
            180                 185                 190

Asp Gly Val Ser Ala Lys Glu Phe Thr Glu Val Ala Asn Arg Trp Leu
        195                 200                 205

Arg Thr Val Ser Trp Phe Met Thr Gly Tyr Ala Asp Gln Ile Asp Thr
    210                 215                 220

Gly Val Tyr Pro Gly Asp Asp Ala Thr Ile Asp Val Gln Val Ala Ala
225                 230                 235                 240

Ile Gly His Leu Leu His Ala Gly Glu Asp Arg Gly Ile Asp Pro Arg
                245                 250                 255

Leu Pro Arg Leu His Leu Glu Leu Met Lys Gly Ala Val Ala Ala Gly
            260                 265                 270

His Gly Gly Asp Ser Tyr Ala Arg Leu Ile Glu Thr Phe Arg Gly Arg
        275                 280                 285

<210> SEQ ID NO 4
<211> LENGTH: 288
<212> TYPE: PRT
<213> ORGANISM: Streptomyces purpureus

<400> SEQUENCE: 4

Met Ala Arg Glu Lys Val Thr Val Ile Gly Leu Gly Arg Met Gly Ser
1               5                   10                  15

Ala Leu Ala Ala Ala Phe Leu Asp Ala Gly His Pro Thr Thr Val Trp
            20                  25                  30

Asn Arg Thr Pro Gly Lys Ala Asp Ala Leu Val Glu Arg Gly Ala Val
        35                  40                  45

Arg Ala Glu Thr Val Ala Val Ala Val Ala Ala Ser Glu Leu Val Val
```

Val Cys Val Leu Asp Tyr Pro Ala Val Arg Asp Leu Leu Ala Pro Val
65                  70                  75                  80

Val Ala Ala Leu Pro Gly Arg Ala Val Val Asn Leu Thr Thr Gly Ser
                85                  90                  95

Pro Glu Gln Ala Arg Glu Ala Ala Trp Ala Ala Gly His Gly Phe
            100                 105                 110

Ala Tyr Leu Asp Gly Ala Val Met Thr Thr Pro Gly Ile Gly Asp
            115                 120                 125

Ser Ala Asn Met Ile Leu Tyr Ser Gly Ala Pro Glu Val Leu Ala Ala
            130                 135                 140

His Arg Asp Ala Leu Ala Val Leu Gly Asp Pro Val Asp Leu Gly Ala
145                 150                 155                 160

Asp Ala Gly Leu Ala Ser Leu Tyr Asp Ala Gly Leu Leu Gly Leu Met
                165                 170                 175

Trp Ser Val Phe Gly Gly Trp Leu His Ala Thr Ala Leu Val Gly Ala
                180                 185                 190

Asp Gly Val Ser Ala Lys Glu Phe Thr Glu Val Ala Asn Arg Trp Leu
                195                 200                 205

Arg Thr Val Ser Trp Phe Met Thr Gly Tyr Ala Asp Gln Ile Asp Thr
            210                 215                 220

Gly Val Tyr Pro Gly Asp Asp Ala Thr Ile Asp Val Gln Val Ala Ala
225                 230                 235                 240

Ile Gly His Leu Leu His Ala Gly Glu Asp Arg Gly Ile Asp Pro Arg
                245                 250                 255

Leu Pro Arg Leu His Leu Glu Leu Met Lys Gly Ala Val Ala Ala Gly
            260                 265                 270

His Gly Gly Asp Ser Tyr Ala Arg Leu Ile Glu Thr Phe Arg Gly Arg
            275                 280                 285

<210> SEQ ID NO 5
<211> LENGTH: 288
<212> TYPE: PRT
<213> ORGANISM: Artificial Sequence
<220> FEATURE:
<223> OTHER INFORMATION: Synthetic peptide sequence

<400> SEQUENCE: 5

Met Ala Arg Glu Lys Val Thr Val Ile Gly Leu Gly Gln Met Gly Ser
1               5                   10                  15

Ala Leu Ala Ala Ala Phe Leu Asp Ala Gly His Pro Thr Thr Val Trp
            20                  25                  30

Asn Arg Thr Pro Gly Lys Ala Asp Ala Leu Val Glu Arg Gly Ala Val
            35                  40                  45

Arg Ala Glu Thr Val Ala Val Ala Val Ala Ala Ser Glu Leu Val Val
50                  55                  60

Val Cys Val Leu Asp Tyr Pro Ala Val Arg Asp Leu Leu Ala Pro Val
65                  70                  75                  80

Val Ala Ala Leu Pro Gly Arg Ala Val Val Asn Leu Thr Thr Gly Ser
                85                  90                  95

Pro Glu Gln Ala Arg Glu Ala Ala Trp Ala Ala Gly His Gly Phe
            100                 105                 110

Ala Tyr Leu Asp Gly Ala Val Met Thr Thr Pro Gly Ile Gly Asp
            115                 120                 125

Ser Ala His Met Ile Leu Tyr Ser Gly Ala Pro Glu Val Leu Ala Ala

```
            130                 135                 140
His Arg Asp Ala Leu Ala Val Leu Gly Asp Pro Val Asp Leu Gly Ala
145                 150                 155                 160

Asp Ala Gly Leu Ala Ser Leu Tyr Asp Ala Gly Leu Leu Gly Leu Met
                165                 170                 175

Trp Ser Val Phe Gly Gly Trp Leu His Ala Thr Ala Leu Val Gly Ala
            180                 185                 190

Asp Gly Val Ser Ala Lys Glu Phe Thr Glu Val Ala Asn Arg Trp Leu
            195                 200                 205

Arg Thr Val Ser Trp Phe Met Thr Gly Tyr Ala Asp Gln Ile Asp Thr
            210                 215                 220

Gly Val Tyr Pro Gly Asp Ala Thr Ile Asp Val Gln Val Ala Ala
225                 230                 235                 240

Ile Gly His Leu Leu His Ala Gly Glu Asp Arg Gly Ile Asp Pro Arg
                245                 250                 255

Leu Pro Arg Leu His Leu Glu Leu Met Lys Gly Ala Val Ala Ala Gly
                260                 265                 270

His Gly Gly Asp Ser Tyr Ala Arg Leu Ile Glu Thr Phe Arg Gly Arg
                275                 280                 285

<210> SEQ ID NO 6
<211> LENGTH: 288
<212> TYPE: PRT
<213> ORGANISM: Artificial Sequence
<220> FEATURE:
<223> OTHER INFORMATION: Synthetic peptide sequence

<400> SEQUENCE: 6

Met Ala Arg Glu Lys Val Thr Val Ile Gly Leu Gly Gln Met Gly Ser
1               5                   10                  15

Ala Leu Ala Ala Ala Phe Leu Asp Ala Gly His Pro Thr Thr Val Trp
                20                  25                  30

Asn Arg Thr Pro Gly Lys Ala Asp Ala Leu Val Glu Arg Gly Ala Val
                35                  40                  45

Arg Ala Glu Thr Val Ala Val Ala Ala Ser Glu Leu Val Val
50                  55                  60

Val Cys Val Leu Asp Tyr Pro Ala Val Arg Asp Leu Leu Ala Pro Val
65                  70                  75                  80

Val Ala Ala Leu Pro Gly Arg Ala Val Asn Leu Thr Thr Gly Ser
                85                  90                  95

Pro Glu Gln Ala Arg Glu Glu Ala Ala Trp Ala Ala Gly His Gly Phe
                100                 105                 110

Ala Tyr Leu Asp Gly Ala Val Met Thr Thr Pro Pro Gly Ile Gly Asp
            115                 120                 125

Ser Ala Asn Met Ile Leu Tyr Ser Gly Ala Pro Glu Val Leu Ala Ala
            130                 135                 140

His Arg Asp Ala Leu Ala Val Leu Gly Asp Pro Val Asp Leu Gly Ala
145                 150                 155                 160

Asp Ala Gly Leu Ala Ser Leu Tyr Asp Met Gly Leu Leu Gly Leu Met
                165                 170                 175

Trp Ser Val Phe Gly Gly Trp Leu His Ala Thr Ala Leu Val Gly Ala
            180                 185                 190

Asp Gly Val Ser Ala Lys Glu Phe Thr Glu Val Ala Asn Arg Trp Leu
            195                 200                 205

Arg Thr Val Ser Trp Phe Met Thr Gly Tyr Ala Asp Gln Ile Asp Thr
```

```
            210                 215                 220

Gly Val Tyr Pro Gly Asp Asp Ala Thr Ile Asp Val Gln Val Ala Ala
225                 230                 235                 240

Ile Gly His Leu Leu His Ala Gly Glu Asp Arg Gly Ile Asp Pro Arg
                245                 250                 255

Leu Pro Arg Leu His Leu Glu Leu Met Lys Gly Ala Val Ala Ala Gly
            260                 265                 270

His Gly Gly Asp Ser Tyr Ala Arg Leu Ile Glu Thr Phe Arg Gly Arg
        275                 280                 285

<210> SEQ ID NO 7
<211> LENGTH: 288
<212> TYPE: PRT
<213> ORGANISM: Artificial Sequence
<220> FEATURE:
<223> OTHER INFORMATION: Synthetic peptide sequence

<400> SEQUENCE: 7

Met Ala Arg Glu Lys Val Thr Val Ile Gly Leu Gly Gln Met Gly Ser
1               5                   10                  15

Ala Leu Ala Ala Ala Phe Leu Asp Ala Gly His Pro Thr Thr Val Trp
                20                  25                  30

Asn Arg Thr Pro Gly Lys Ala Asp Ala Leu Val Glu Arg Gly Ala Val
            35                  40                  45

Arg Ala Glu Thr Val Ala Val Ala Val Ala Ala Ser Glu Leu Val Val
        50                  55                  60

Val Cys Val Leu Asp Tyr Pro Ala Val Arg Asp Leu Leu Ala Pro Val
65                  70                  75                  80

Val Ala Ala Leu Pro Gly Arg Ala Val Val Asn Leu Thr Thr Gly Ser
                85                  90                  95

Pro Glu Gln Ala Arg Glu Gly Ala Ala Trp Ala Ala Gly His Gly Phe
            100                 105                 110

Ala Tyr Leu Asp Gly Ala Val Met Thr Thr Pro Pro Gly Ile Gly Asp
        115                 120                 125

Ser Ala Asn Met Ile Leu Tyr Ser Gly Ala Pro Glu Val Leu Ala Ala
130                 135                 140

His Arg Asp Ala Leu Ala Val Leu Gly Asp Pro Val Asp Leu Gly Ala
145                 150                 155                 160

Asp Ala Gly Leu Ala Ser Leu Tyr Asp Ala Gly Leu Leu Gly Leu Met
                165                 170                 175

Trp Ser Val Met Gly Gly Trp Leu His Ala Thr Ala Leu Val Gly Ala
            180                 185                 190

Asp Gly Val Ser Ala Lys Glu Phe Thr Glu Val Ala Asn Arg Trp Leu
        195                 200                 205

Arg Thr Val Ser Trp Phe Met Thr Gly Tyr Ala Asp Gln Ile Asp Thr
210                 215                 220

Gly Val Tyr Pro Gly Asp Asp Ala Thr Ile Asp Val Gln Val Ala Ala
225                 230                 235                 240

Ile Gly His Leu Leu His Ala Gly Glu Asp Arg Gly Ile Asp Pro Arg
                245                 250                 255

Leu Pro Arg Leu His Leu Glu Leu Met Lys Gly Ala Val Ala Ala Gly
            260                 265                 270

His Gly Gly Asp Ser Tyr Ala Arg Leu Ile Glu Thr Phe Arg Gly Arg
        275                 280                 285
```

```
<210> SEQ ID NO 8
<211> LENGTH: 288
<212> TYPE: PRT
<213> ORGANISM: Artificial Sequence
<220> FEATURE:
<223> OTHER INFORMATION: Synthetic peptide sequence

<400> SEQUENCE: 8
```

Met Ala Arg Glu Lys Val Thr Val Ile Gly Leu Gly Arg Met Gly Ser
1               5                   10                  15

Ala Leu Ala Ala Ala Phe Leu Asp Ala Gly His Pro Thr Thr Val Trp
                20                  25                  30

Asn Arg Thr Pro Gly Lys Ala Asp Ala Leu Val Glu Arg Gly Ala Val
            35                  40                  45

Arg Ala Glu Thr Val Ala Val Ala Val Ala Ala Ser Glu Leu Val Val
        50                  55                  60

Val Cys Val Leu Asp Tyr Pro Ala Val Arg Asp Leu Leu Ala Pro Val
65                  70                  75                  80

Val Ala Ala Leu Pro Gly Arg Ala Val Val Asn Leu Thr Thr Gly Ser
                85                  90                  95

Pro Glu Gln Ala Arg Glu Glu Ala Ala Trp Ala Ala Gly His Gly Phe
            100                 105                 110

Ala Tyr Leu Asp Gly Ala Val Met Thr Thr Pro Pro Gly Ile Gly Asp
        115                 120                 125

Ser Ala Asn Met Ile Leu Tyr Ser Gly Ala Pro Glu Val Leu Ala Ala
130                 135                 140

His Arg Asp Ala Leu Ala Val Leu Gly Asp Pro Val Asp Leu Gly Ala
145                 150                 155                 160

Asp Ala Gly Leu Ala Ser Leu Tyr Asp Ala Gly Leu Leu Gly Leu Met
                165                 170                 175

Trp Ser Val Phe Gly Gly Trp Leu His Ala Thr Ala Leu Val Gly Ala
            180                 185                 190

Asp Gly Val Ser Ala Lys Glu Phe Thr Glu Val Ala Asn Arg Trp Leu
        195                 200                 205

Arg Thr Val Ser Trp Ile Met Thr Gly Tyr Ala Asp Gln Ile Asp Thr
    210                 215                 220

Gly Val Tyr Pro Gly Asp Asp Ala Thr Ile Asp Val Gln Val Ala Ala
225                 230                 235                 240

Ile Gly His Leu Leu His Ala Gly Glu Asp Arg Gly Ile Asp Pro Arg
                245                 250                 255

Leu Pro Arg Leu His Leu Glu Leu Met Lys Gly Ala Val Ala Ala Gly
            260                 265                 270

His Gly Gly Asp Ser Tyr Ala Arg Leu Ile Glu Thr Phe Arg Gly Arg
        275                 280                 285

```
<210> SEQ ID NO 9
<211> LENGTH: 288
<212> TYPE: PRT
<213> ORGANISM: Artificial Sequence
<220> FEATURE:
<223> OTHER INFORMATION: Synthetic peptide sequence

<400> SEQUENCE: 9
```

Met Ala Arg Glu Lys Val Thr Val Ile Gly Leu Gly Arg Met Gly Ser
1               5                   10                  15

Ala Leu Ala Ala Ala Phe Leu Asp Ala Gly His Pro Thr Thr Val Trp
                20                  25                  30

-continued

```
Asn Arg Thr Pro Gly Lys Ala Asp Ala Leu Val Glu Arg Gly Ala Val
         35                  40                  45
Arg Ala Glu Thr Val Ala Val Ala Val Ala Ala Ser Glu Leu Val Val
 50                  55                  60
Val Cys Val Leu Asp Tyr Pro Ala Val Arg Asp Leu Leu Ala Pro Val
 65                  70                  75                  80
Val Ala Ala Leu Pro Gly Arg Ala Val Val Asn Leu Thr Thr Gly Ser
                 85                  90                  95
Pro Glu Gln Ala Arg Glu Glu Ala Ala Trp Ala Ala Gly His Gly Phe
                100                 105                 110
Ala Tyr Leu Asp Gly Ala Val Met Thr Thr Pro Gly Ile Gly Asp
         115                 120                 125
Ser Ala Asn Met Ile Leu Tyr Ser Gly Ala Pro Glu Val Leu Ala Ala
     130                 135                 140
His Arg Asp Ala Leu Ala Val Leu Gly Asp Pro Val Asp Leu Gly Ala
145                 150                 155                 160
Asp Ala Gly Leu Ala Ser Leu Tyr Asp Met Gly Leu Leu Gly Leu Met
                165                 170                 175
Trp Ser Val Phe Gly Gly Trp Leu His Ala Thr Ala Leu Val Gly Ala
            180                 185                 190
Asp Gly Val Ser Ala Lys Glu Phe Thr Glu Val Ala Asn Arg Trp Leu
        195                 200                 205
Arg Thr Val Ser Trp Phe Met Thr Gly Tyr Ala Asp Gln Ile Asp Thr
    210                 215                 220
Gly Val Tyr Pro Gly Asp Asp Ala Thr Ile Asp Val Gln Val Ala Ala
225                 230                 235                 240
Ile Gly His Leu Leu His Ala Gly Glu Asp Arg Gly Ile Asp Pro Arg
                245                 250                 255
Leu Pro Arg Leu His Leu Glu Leu Met Lys Gly Ala Val Ala Ala Gly
            260                 265                 270
His Gly Gly Asp Ser Tyr Ala Arg Leu Ile Glu Thr Phe Arg Gly Arg
        275                 280                 285

<210> SEQ ID NO 10
<211> LENGTH: 288
<212> TYPE: PRT
<213> ORGANISM: Artificial Sequence
<220> FEATURE:
<223> OTHER INFORMATION: Synthetic peptide sequence

<400> SEQUENCE: 10

Met Ala Arg Glu Lys Val Thr Val Ile Gly Leu Gly Arg Met Gly Ser
 1               5                  10                  15
Ala Leu Ala Ala Ala Phe Leu Asp Ala Gly His Pro Thr Thr Val Trp
                 20                  25                  30
Asn Arg Thr Pro Gly Lys Ala Asp Ala Leu Val Glu Arg Gly Ala Val
         35                  40                  45
Arg Ala Glu Thr Val Ala Val Ala Val Ala Ala Ser Glu Leu Val Val
     50                  55                  60
Val Cys Val Leu Asp Tyr Pro Ala Val Arg Asp Leu Leu Ala Pro Val
 65                  70                  75                  80
Val Ala Ala Leu Pro Gly Arg Ala Val Val Asn Leu Thr Thr Gly Ser
                 85                  90                  95
Pro Glu Gln Ala Arg Glu Glu Ala Ala Trp Ala Ala Gly His Gly Phe
                100                 105                 110
```

```
Ala Tyr Leu Asp Gly Ala Val Met Thr Thr Pro Gly Ile Gly Asp
        115                 120                 125

Ser Ala Asn Met Ile Leu Tyr Ser Gly Ala Pro Glu Val Leu Ala Ala
    130                 135                 140

His Arg Asp Ala Leu Ala Val Leu Gly Asp Pro Val Asp Leu Gly Ala
145                 150                 155                 160

Asp Ala Gly Leu Ala Ser Leu Tyr Asp Ala Gly Leu Leu Gly Leu Met
                165                 170                 175

Trp Ser Val Phe Gly Gly Trp Leu His Ala Thr Ala Leu Val Gly Ala
            180                 185                 190

Asp Gly Val Ser Ala Lys Glu Phe Thr Glu Val Ala Asn Arg Trp Leu
        195                 200                 205

Arg Thr Val Ser Trp Ile Met Thr Gly Tyr Ala Asp Gln Ile Asp Thr
    210                 215                 220

Gly Val Tyr Pro Gly Asp Asp Ala Thr Ile Asp Val Gln Val Ala Ala
225                 230                 235                 240

Ile Gly His Leu Leu His Ala Gly Glu Asp Arg Gly Ile Asp Pro Arg
                245                 250                 255

Leu Pro Arg Leu His Leu Glu Leu Met Lys Gly Ala Val Ala Ala Gly
            260                 265                 270

His Gly Gly Asp Ser Tyr Ala Arg Leu Ile Glu Thr Phe Arg Gly Arg
        275                 280                 285

<210> SEQ ID NO 11
<211> LENGTH: 288
<212> TYPE: PRT
<213> ORGANISM: Artificial Sequence
<220> FEATURE:
<223> OTHER INFORMATION: Synthetic peptide sequence

<400> SEQUENCE: 11

Met Ala Arg Glu Lys Val Thr Val Ile Gly Leu Gly Gln Met Gly Ser
1               5                   10                  15

Ala Leu Ala Ala Ala Phe Leu Asp Ala Gly His Pro Thr Thr Val Trp
                20                  25                  30

Asn Arg Thr Pro Gly Lys Ala Asp Ala Leu Val Glu Arg Gly Ala Val
            35                  40                  45

Arg Ala Glu Thr Val Ala Val Ala Val Ala Ser Glu Leu Val Val
        50                  55                  60

Val Cys Val Leu Asp Tyr Pro Ala Val Arg Asp Leu Leu Ala Pro Val
65                  70                  75                  80

Val Ala Ala Leu Pro Gly Arg Ala Val Val Asn Leu Thr Thr Gly Ser
                85                  90                  95

Pro Glu Gln Ala Arg Glu Glu Ala Ala Trp Ala Ala Gly His Gly Phe
            100                 105                 110

Ala Tyr Leu Asp Gly Ala Val Met Thr Thr Pro Pro Gly Ile Gly Asp
        115                 120                 125

Ser Ala His Met Ile Leu Tyr Ser Gly Ala Pro Glu Val Leu Ala Ala
    130                 135                 140

His Arg Asp Ala Leu Ala Val Leu Gly Asp Pro Val Asp Leu Gly Ala
145                 150                 155                 160

Asp Ala Gly Leu Ala Ser Leu Tyr Asp Cys Gly Leu Leu Gly Leu Met
                165                 170                 175

Trp Ser Val Met Gly Gly Trp Leu His Ala Thr Ala Leu Val Gly Ala
            180                 185                 190
```

```
Asp Gly Val Ser Ala Lys Glu Phe Thr Glu Val Ala Asn Arg Trp Leu
            195                 200                 205

Arg Thr Val Ser Trp Phe Met Thr Gly Tyr Ala Asp Gln Ile Asp Thr
210                 215                 220

Gly Val Tyr Pro Gly Asp Asp Ala Thr Ile Asp Val Gln Val Ala Ala
225                 230                 235                 240

Ile Gly His Leu Leu His Ala Gly Glu Asp Arg Gly Ile Asp Pro Arg
            245                 250                 255

Leu Pro Arg Leu His Leu Glu Leu Met Lys Gly Ala Val Ala Ala Gly
            260                 265                 270

His Gly Gly Asp Ser Tyr Ala Arg Leu Ile Glu Thr Phe Arg Gly Arg
            275                 280                 285
```

<210> SEQ ID NO 12
<211> LENGTH: 288
<212> TYPE: PRT
<213> ORGANISM: Artificial Sequence
<220> FEATURE:
<223> OTHER INFORMATION: Synthetic peptide sequence

<400> SEQUENCE: 12

```
Met Ala Arg Glu Lys Val Thr Val Ile Gly Leu Gly Arg Met Gly Ser
1               5                   10                  15

Ala Leu Ala Ala Ala Phe Leu Asp Ala Gly His Pro Thr Thr Val Trp
            20                  25                  30

Asn Arg Thr Pro Gly Lys Ala Asp Ala Leu Val Glu Arg Gly Ala Val
            35                  40                  45

Arg Ala Glu Thr Val Ala Val Ala Ala Ser Glu Leu Val Val
50                  55                  60

Val Cys Val Leu Asp Tyr Pro Ala Val Arg Asp Leu Leu Ala Pro Val
65                  70                  75                  80

Val Ala Ala Leu Pro Gly Arg Ala Val Asn Leu Thr Thr Gly Ser
            85                  90                  95

Pro Glu Gln Ala Arg Glu Gly Ala Ala Trp Ala Ala Gly His Gly Phe
            100                 105                 110

Ala Tyr Leu Asp Gly Ala Val Met Thr Thr Pro Pro Gly Ile Gly Asp
            115                 120                 125

Ser Ala His Met Ile Leu Tyr Ser Gly Ala Pro Glu Val Leu Ala Ala
            130                 135                 140

His Arg Asp Ala Leu Ala Val Leu Gly Asp Pro Val Asp Leu Gly Ala
145                 150                 155                 160

Asp Ala Gly Leu Ala Ser Leu Tyr Asp Cys Gly Leu Leu Gly Leu Met
                165                 170                 175

Trp Ser Val Phe Gly Gly Trp Leu His Ala Thr Ala Leu Val Gly Ala
            180                 185                 190

Asp Gly Val Ser Ala Lys Glu Phe Thr Glu Val Ala Asn Arg Trp Leu
            195                 200                 205

Arg Thr Val Ser Trp Asn Met Thr Gly Tyr Ala Asp Gln Ile Asp Thr
210                 215                 220

Gly Val Tyr Pro Gly Asp Asp Ala Thr Ile Asp Val Gln Val Ala Ala
225                 230                 235                 240

Ile Gly His Leu Leu His Ala Gly Glu Asp Arg Gly Ile Asp Pro Arg
            245                 250                 255

Leu Pro Arg Leu His Leu Glu Leu Met Lys Gly Ala Val Ala Ala Gly
            260                 265                 270
```

His Gly Gly Asp Ser Tyr Ala Arg Leu Ile Glu Thr Phe Arg Gly Arg
            275                 280                 285

<210> SEQ ID NO 13
<211> LENGTH: 288
<212> TYPE: PRT
<213> ORGANISM: Artificial Sequence
<220> FEATURE:
<223> OTHER INFORMATION: Synthetic peptide sequence

<400> SEQUENCE: 13

Met Ala Arg Glu Lys Val Thr Val Ile Gly Leu Gly Arg Met Gly Ser
1               5                   10                  15

Ala Leu Ala Ala Ala Phe Leu Asp Ala Gly His Pro Thr Thr Val Trp
            20                  25                  30

Asn Arg Thr Pro Gly Lys Ala Asp Ala Leu Val Glu Arg Gly Ala Val
        35                  40                  45

Arg Ala Glu Thr Val Ala Val Ala Ala Ser Glu Leu Val Val
    50                  55                  60

Val Cys Val Leu Asp Tyr Pro Ala Val Arg Asp Leu Leu Ala Pro Val
65                  70                  75                  80

Val Ala Ala Leu Pro Gly Arg Ala Val Val Asn Leu Thr Thr Gly Ser
                85                  90                  95

Pro Glu Gln Ala Arg Glu Glu Ala Ala Trp Ala Ala Gly His Gly Phe
            100                 105                 110

Ala Tyr Leu Asp Gly Ala Val Met Thr Thr Pro Pro Gly Ile Gly Asp
        115                 120                 125

Ser Ala His Met Ile Leu Tyr Ser Gly Ala Pro Glu Val Leu Ala Ala
    130                 135                 140

His Arg Asp Ala Leu Ala Val Leu Gly Asp Pro Val Asp Leu Gly Ala
145                 150                 155                 160

Asp Ala Gly Leu Ala Ser Leu Tyr Asp Cys Gly Leu Leu Gly Leu Met
                165                 170                 175

Trp Ser Val Met Gly Gly Trp Leu His Ala Thr Ala Leu Val Gly Ala
            180                 185                 190

Asp Gly Val Ser Ala Lys Glu Phe Thr Glu Val Ala Asn Arg Trp Leu
        195                 200                 205

Arg Thr Val Ser Trp Phe Met Thr Gly Tyr Ala Asp Gln Ile Asp Thr
    210                 215                 220

Gly Val Tyr Pro Gly Asp Asp Ala Thr Ile Asp Val Gln Val Ala Ala
225                 230                 235                 240

Ile Gly His Leu Leu His Ala Gly Glu Asp Arg Gly Ile Asp Pro Arg
                245                 250                 255

Leu Pro Arg Leu His Leu Glu Leu Met Lys Gly Ala Val Ala Ala Gly
            260                 265                 270

His Gly Gly Asp Ser Tyr Ala Arg Leu Ile Glu Thr Phe Arg Gly Arg
        275                 280                 285

<210> SEQ ID NO 14
<211> LENGTH: 288
<212> TYPE: PRT
<213> ORGANISM: Artificial Sequence
<220> FEATURE:
<223> OTHER INFORMATION: Synthetic peptide sequence

<400> SEQUENCE: 14

Met Ala Arg Glu Lys Val Thr Val Ile Gly Leu Gly Gln Met Gly Ser
1               5                   10                  15

```
Ala Leu Ala Ala Ala Phe Leu Asp Ala Gly His Pro Thr Thr Val Trp
            20                  25                  30

Asn Arg Thr Pro Gly Lys Ala Asp Ala Leu Val Glu Arg Gly Ala Val
        35                  40                  45

Arg Ala Glu Thr Val Ala Val Ala Val Ala Ala Ser Glu Leu Val Val
    50                  55                  60

Val Cys Val Leu Asp Tyr Pro Ala Val Arg Asp Leu Leu Ala Pro Val
65                  70                  75                  80

Val Ala Ala Leu Pro Gly Arg Ala Val Val Asn Leu Thr Thr Gly Ser
                85                  90                  95

Pro Glu Gln Ala Arg Glu Ala Ala Trp Ala Ala Gly His Gly Phe
            100                 105                 110

Ala Tyr Leu Asp Gly Ala Val Met Thr Thr Pro Gly Ile Gly Asp
        115                 120                 125

Ser Ala His Met Ile Leu Tyr Ser Gly Ala Pro Glu Val Leu Ala Ala
    130                 135                 140

His Arg Asp Ala Leu Ala Val Leu Gly Asp Pro Val Asp Leu Gly Ala
145                 150                 155                 160

Asp Ala Gly Leu Ala Ser Leu Tyr Asp Cys Gly Leu Leu Gly Leu Met
                165                 170                 175

Trp Ser Val Met Gly Gly Trp Leu His Ala Thr Ala Leu Val Gly Ala
            180                 185                 190

Asp Gly Val Ser Ala Lys Glu Phe Thr Glu Val Ala Asn Arg Trp Leu
        195                 200                 205

Arg Thr Val Ser Trp Phe Met Thr Asp Tyr Ala Asp Gln Ile Asp Thr
    210                 215                 220

Gly Val Tyr Pro Gly Asp Asp Ala Thr Ile Asp Val Gln Val Ala Ala
225                 230                 235                 240

Ile Gly His Leu Leu His Ala Gly Glu Asp Arg Gly Ile Asp Pro Arg
                245                 250                 255

Leu Pro Arg Leu His Leu Glu Leu Met Lys Gly Ala Val Ala Ala Gly
            260                 265                 270

His Gly Gly Asp Ser Tyr Ala Arg Leu Ile Glu Thr Phe Arg Gly Arg
        275                 280                 285

<210> SEQ ID NO 15
<211> LENGTH: 288
<212> TYPE: PRT
<213> ORGANISM: Artificial Sequence
<220> FEATURE:
<223> OTHER INFORMATION: Synthetic peptide sequence

<400> SEQUENCE: 15

Met Ala Arg Glu Lys Val Thr Val Ile Gly Leu Gly Arg Met Gly Ser
1               5                   10                  15

Ala Leu Ala Ala Ala Phe Leu Asp Ala Gly His Pro Thr Thr Val Trp
            20                  25                  30

Asn Arg Thr Pro Gly Lys Ala Asp Ala Leu Val Glu Arg Gly Ala Val
        35                  40                  45

Arg Ala Glu Thr Val Ala Val Ala Val Ala Ala Ser Glu Leu Val Val
    50                  55                  60

Val Cys Val Leu Asp Tyr Pro Ala Val Arg Asp Leu Leu Ala Pro Val
65                  70                  75                  80

Val Ala Ala Leu Pro Gly Arg Ala Val Val Asn Leu Thr Thr Gly Ser
                85                  90                  95
```

```
Pro Glu Gln Ala Arg Glu Glu Ala Ala Trp Ala Ala Gly His Gly Phe
            100                 105                 110
Ala Tyr Leu Asp Gly Ala Val Met Thr Thr Pro Pro Gly Ile Gly Asp
            115                 120                 125
Ser Ala His Met Ile Leu Tyr Ser Gly Ala Pro Glu Val Leu Ala Ala
            130                 135                 140
His Arg Asp Ala Leu Ala Val Leu Gly Asp Pro Val Asp Leu Gly Ala
145                 150                 155                 160
Asp Ala Gly Leu Ala Ser Leu Tyr Asp Cys Gly Leu Leu Gly Leu Met
                165                 170                 175
Trp Ser Val Met Gly Gly Trp Leu His Ala Thr Ala Leu Val Gly Ala
            180                 185                 190
Asp Gly Val Ser Ala Lys Glu Phe Thr Glu Val Ala Asn Arg Trp Leu
            195                 200                 205
Arg Thr Val Ser Trp Asn Met Thr Gly Tyr Ala Arg Gln Ile Asp Thr
    210                 215                 220
Gly Val Tyr Pro Gly Asp Asp Ala Thr Ile Asp Val Gln Val Ala Ala
225                 230                 235                 240
Ile Gly His Leu Leu His Ala Gly Glu Asp Arg Gly Ile Asp Pro Arg
                245                 250                 255
Leu Pro Arg Leu His Leu Glu Leu Met Lys Gly Ala Val Ala Ala Gly
            260                 265                 270
His Gly Gly Asp Ser Tyr Ala Arg Leu Ile Glu Thr Phe Arg Gly Arg
            275                 280                 285
```